(12) United States Patent
Nielsen et al.

(10) Patent No.: US 8,684,916 B2
(45) Date of Patent: Apr. 1, 2014

(54) INDUCTION COIL SENSING

(75) Inventors: Per Gorm Gunther Nielsen, New South Wales (AU); Michael Gunther Nielsen, New South Wales (AU); John Ross Le Strange, New South Wales (AU)

(73) Assignee: Techmin Pty Limited (AU)

( * ) Notice: Subject to any disclaimer, the term of this patent is extended or adjusted under 35 U.S.C. 154(b) by 1129 days.

(21) Appl. No.: 12/158,311

(22) PCT Filed: Dec. 19, 2006

(86) PCT No.: PCT/AU2006/001935
§ 371 (c)(1),
(2), (4) Date: Dec. 17, 2008

(87) PCT Pub. No.: WO2007/070943
PCT Pub. Date: Jun. 28, 2007

(65) Prior Publication Data
US 2009/0209816 A1      Aug. 20, 2009

(30) Foreign Application Priority Data

Dec. 19, 2005   (AU) .............................. 2005907148

(51) Int. Cl.
*A61B 1/267*        (2006.01)
(52) U.S. Cl.
USPC ............ 600/185; 600/193; 600/197; 600/199
(58) Field of Classification Search
USPC .................................................. 600/185–199
See application file for complete search history.

(56) References Cited

U.S. PATENT DOCUMENTS

| 4,605,268 | A |   | 8/1986  | Meador |
| 5,070,737 | A | * | 12/1991 | Reilly ....................... 73/862.046 |
| 5,502,295 | A | * | 3/1996  | Owen et al. .................... 235/380 |
| 5,536,245 | A | * | 7/1996  | Dahlbeck ....................... 600/195 |
| 5,545,187 | A | * | 8/1996  | Bergstrom et al. ............. 607/32 |
| 5,587,573 | A | * | 12/1996 | Owen et al. .................... 235/380 |
| 5,849,020 | A |   | 12/1998 | Long et al. |
| 5,895,360 | A | * | 4/1999  | Christopherson et al. .... 600/529 |
| 5,944,680 | A | * | 8/1999  | Christopherson et al. ...... 602/42 |
| 6,021,352 | A | * | 2/2000  | Christopherson et al. ...... 607/42 |

(Continued)

FOREIGN PATENT DOCUMENTS

| DE | 10066004 A1 | 12/2001 |
| DE | 10065705 A1 | 1/2002 |

(Continued)

OTHER PUBLICATIONS

Supplementary European Search Report dated Jul. 29, 2011.

*Primary Examiner* — Ellen C Hammond
*Assistant Examiner* — Stuart S Bray
(74) *Attorney, Agent, or Firm* — Bryan Cave LLP

(57) ABSTRACT

Disclosed is apparatus (110) comprising a first device (120) adapted to be releasably operatively coupled to a second device (130). The second device comprises a detection coil (136) associated with a coupling arrangement (133) of the second device. The first device comprises a sensing coil (2206) arranged at a coupling region (123) of the first device, the coupling region being operatively associable with the coupling arrangement of the second device. The apparatus also has a circuit (125) connected to the sensing coil and configured to detect at least coupling of the first device to the second device through interaction of the detection coil with an electrical signal imparted upon the sensing coil.

18 Claims, 29 Drawing Sheets

(56) References Cited

U.S. PATENT DOCUMENTS

| | | | |
|---|---|---|---|
| 6,027,473 A * | 2/2000 | Ponzi | 604/528 |
| 6,099,479 A * | 8/2000 | Christopherson et al. | 600/529 |
| 6,132,384 A * | 10/2000 | Christopherson et al. | 600/529 |
| 6,200,256 B1 * | 3/2001 | Weinberger | 600/3 |
| 6,496,713 B2 * | 12/2002 | Avrin et al. | 600/409 |
| 6,572,543 B1 * | 6/2003 | Christopherson et al. | 600/300 |
| 6,655,377 B2 * | 12/2003 | Pacey | 128/200.26 |
| 6,676,598 B2 | 1/2004 | Rudischhauser et al. | |
| 7,102,354 B2 * | 9/2006 | Ardenkjaer-Larsen et al. | 324/321 |
| 7,372,274 B2 * | 5/2008 | Ardenkjaer-Larsen et al. | 324/321 |
| 7,462,157 B2 * | 12/2008 | Jarrell | 600/591 |
| 7,528,597 B2 * | 5/2009 | Taylor et al. | 324/207.15 |
| 7,720,521 B2 * | 5/2010 | Chang et al. | 600/424 |
| 7,970,477 B2 * | 6/2011 | Loeb et al. | 607/48 |
| 7,976,481 B2 * | 7/2011 | Jarrell | 600/591 |
| 8,106,657 B2 * | 1/2012 | Sakellariou et al. | 324/321 |
| 2003/0101526 A1 | 6/2003 | Hilscher et al. | |
| 2003/0200814 A1 | 10/2003 | Oh et al. | |
| 2004/0049108 A1 * | 3/2004 | Ardenkjaer-Larsen et al. | 600/412 |
| 2004/0066193 A1 * | 4/2004 | Ardenkjaer-Larsen et al. | 324/309 |
| 2004/0122292 A1 * | 6/2004 | Dey et al. | 600/190 |
| 2005/0059863 A1 * | 3/2005 | Zilch | 600/188 |
| 2005/0187434 A1 * | 8/2005 | Dey et al. | 600/179 |
| 2005/0203365 A1 * | 9/2005 | Jarrell | 600/373 |
| 2005/0225328 A1 * | 10/2005 | Ardenkjaer-Larsen et al. | 324/321 |
| 2005/0237197 A1 * | 10/2005 | Liebermann et al. | 340/572.6 |
| 2006/0241399 A1 * | 10/2006 | Fabian | 600/424 |
| 2007/0270722 A1 * | 11/2007 | Loeb et al. | 600/595 |
| 2008/0136410 A1 * | 6/2008 | Song et al. | 324/303 |
| 2008/0146879 A1 * | 6/2008 | Pacey | 600/188 |
| 2009/0043174 A1 * | 2/2009 | Jarrell | 600/300 |
| 2010/0156414 A1 * | 6/2010 | Sakellariou et al. | 324/309 |

FOREIGN PATENT DOCUMENTS

| | | |
|---|---|---|
| EP | 1197186 A1 | 4/2002 |
| EP | 1433413 A2 | 6/2004 |
| WO | WO 00/10456 A1 | 3/2000 |
| WO | WO 02/071930 A1 | 9/2002 |
| WO | 03042499 | 5/2003 |
| WO | WO 03/042499 A1 | 5/2003 |

* cited by examiner

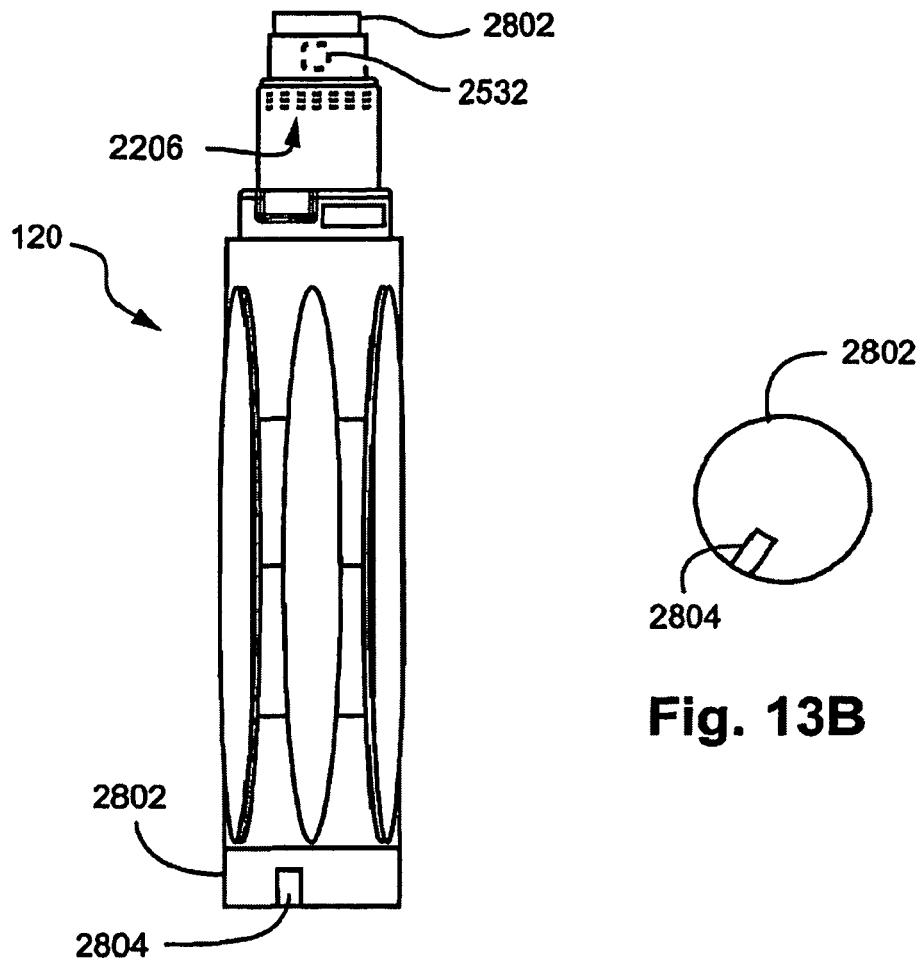
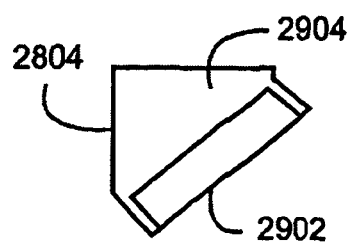
Fig. 14A
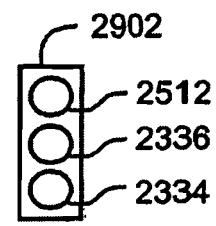
Fig. 14B

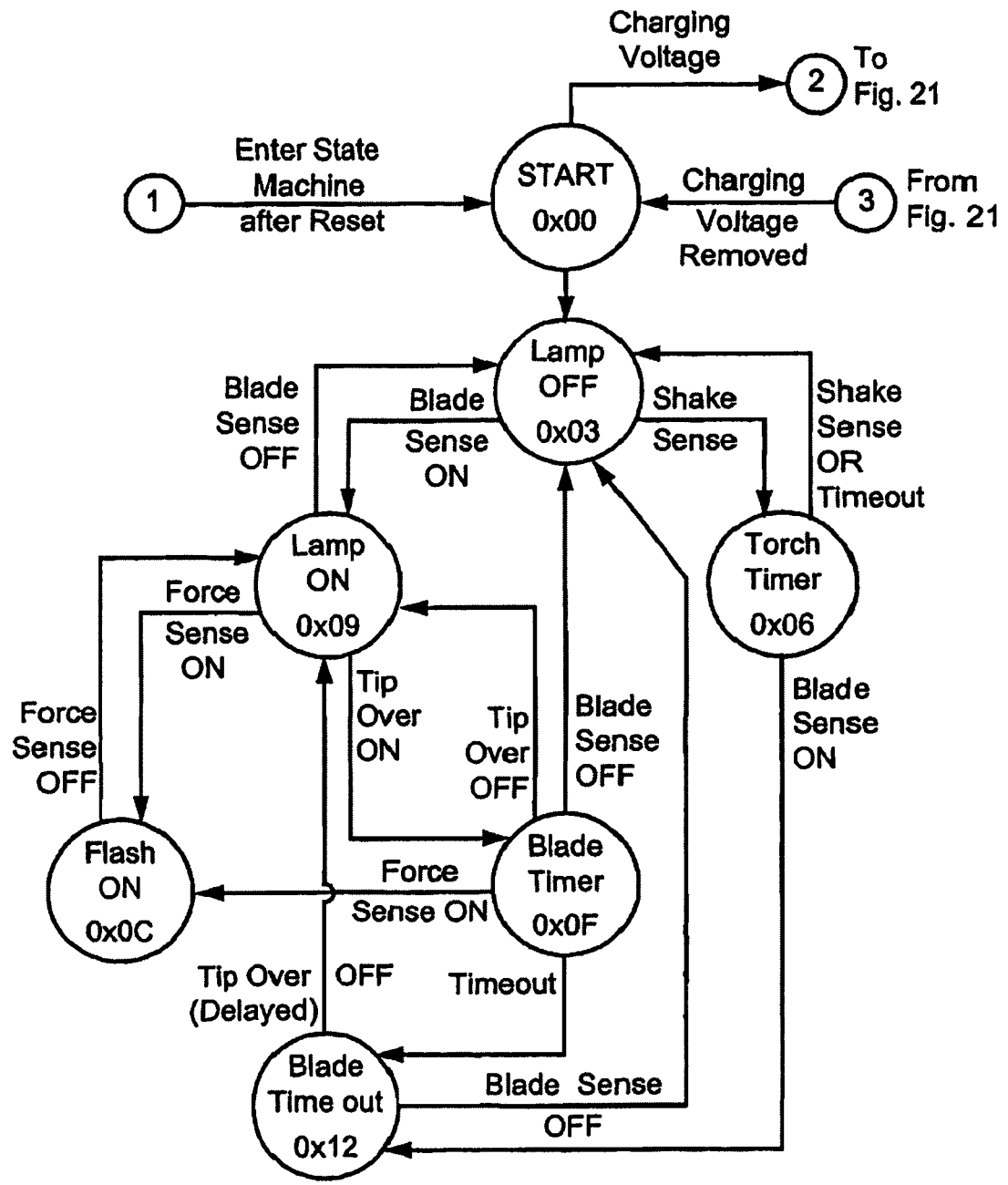
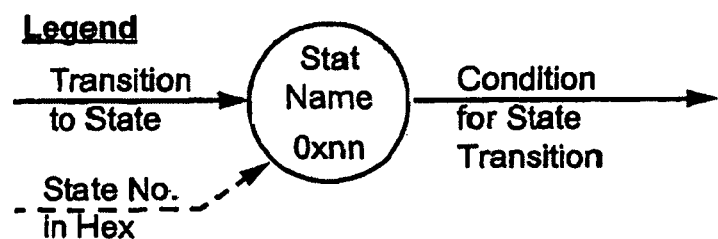
Fig. 20

Torch and Blade Timing Delay

Shock Switch Timing Delay

Shock Switch Interrupt Service Routine

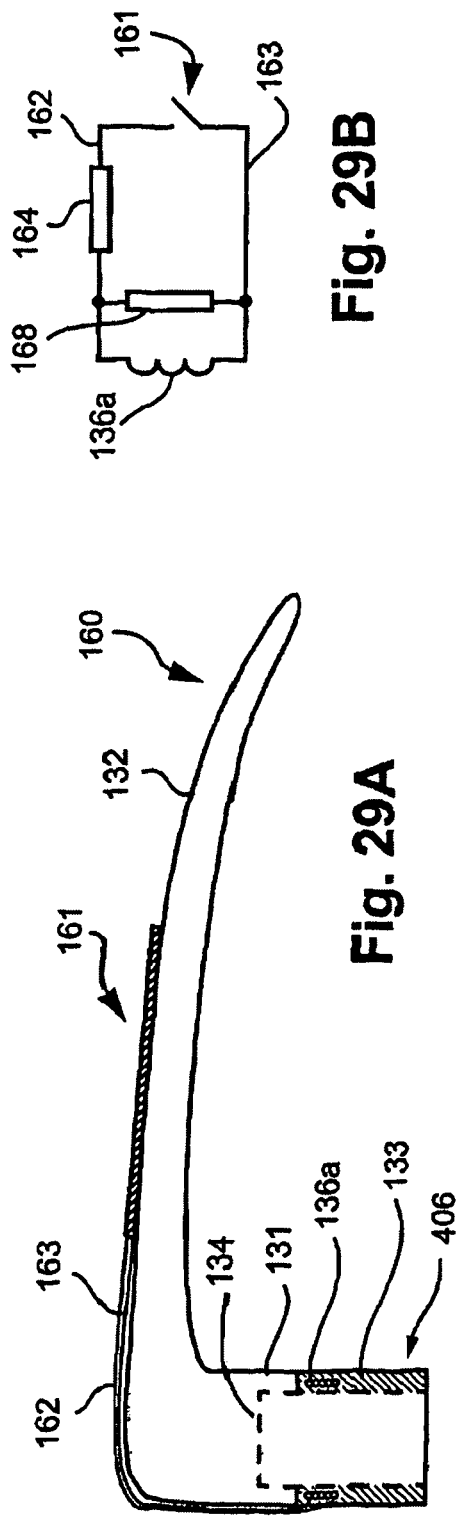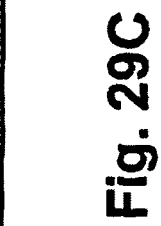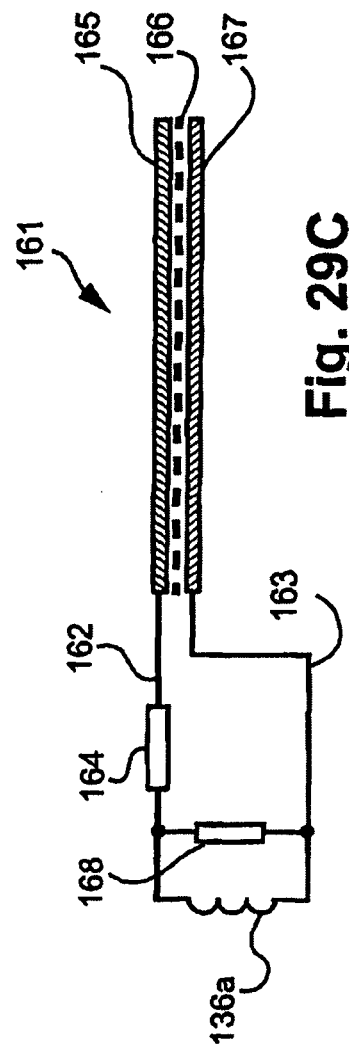

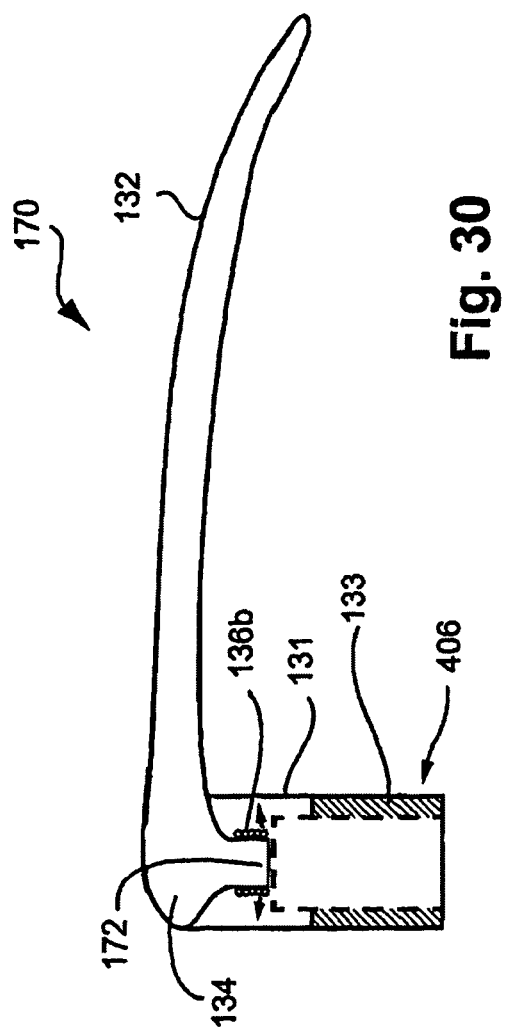

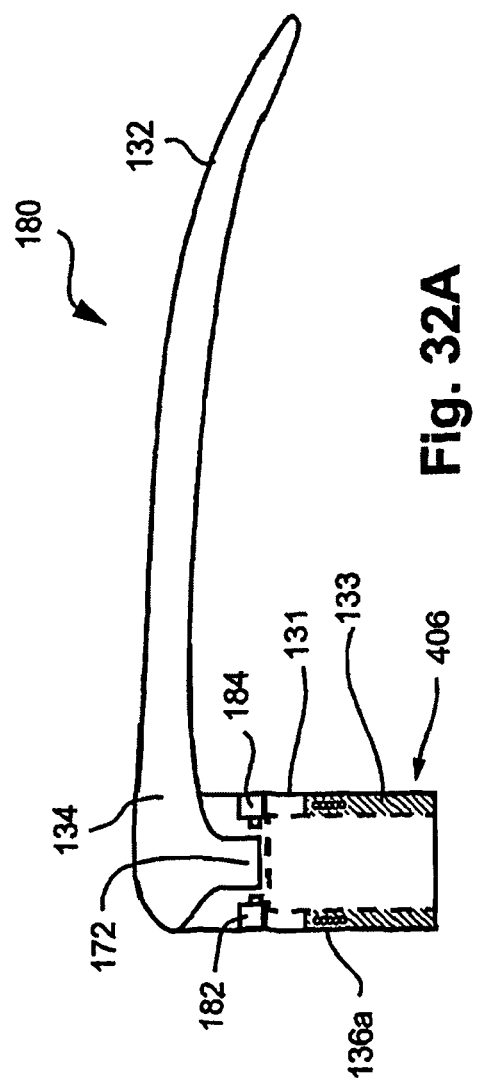
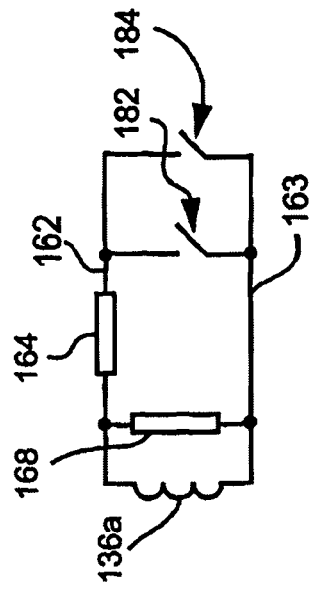

INDUCTION COIL SENSING

This application is the National Stage of International Application No. PCT/AU2006/001935, filed Nov. 19, 2006, which claims priority from Australian Patent Application No. 2005/907148, filed Dec. 19, 2005.

TECHNICAL FIELD

The present invention relates to electrical apparatus having components adapted to be coupled which have significantly different structures, one of which may be of a single-use, disposable nature. More particularly, the present invention is concerned with the electrical operation of such apparatus and by which the coupling affords the electrical operation.

BACKGROUND

A laryngoscope is a medical implement comprising an elongate handle releasably connectable to an arcuate blade that is adapted for insertion into a patient's throat. Such a device is useful for intubation of a patient. The blade is connected to the handle by rotating the blade upwardly with respect to the handle. The handle is hollow and contains batteries for powering a light source to provide illumination to a distal end of the blade. The light source is traditionally an incandescent lamp arranged in the blade.

Historically, the handle and blade have been formed from metal to provide the stiffness required for opening a patient's airway. Accordingly, these known laryngoscopes have a high capital cost, and are therefore sterilised and reused many times during their service life. The typical cleaning method is autoclaving, which is in itself expensive.

In recent years, concern has been raised as to the adequacy of the cleaning and sterilisation of laryngoscopes. It is noted that metal laryngoscope handles are particularly difficult to clean, as they are often knurled, which provides a multitude of locations for bacteria and other contaminants to avoid sterilisation. In an attempt to address this problem, some disposable blade laryngoscopes have been developed. However, known disposable blade laryngoscopes have retained the same connection system as for the older fully reusable, metal laryngoscopes, in that the blade is rotated upwardly with respect to the handle to engage the blade to the handle. When the disposable blades are connected to the handle in this manner, the blade tip can often touch the handle, and accordingly, contaminants present on the handle can be transferred to the blade and subsequently to the patient.

Another problem with known disposable blades is that they often lack means for preventing their accidental re-use. Where means for preventing blade re-use are provided, it is often only apparent after a user has attempted several times to connect the blade to the handle that it is realised that the blade in hand is a used blade, thereby causing user frustration and time delays. As will be appreciated, such frustration and delays can be critical in many instances where laryngoscopes are required.

The desirability of single-use disposable blades introduces more problems including appropriate powering of the lamp and electrical connection thereto, together with reducing cost of manufacture of the disposable blade.

SUMMARY

It is an object of the present invention to substantially overcome or at least ameliorate one or more problems of prior art devices, or at least to provide a useful alternative.

The described arrangements, whilst specifically adapted for laryngoscopes, may be readily adapted for other apparatus and devices. One such example is an endoscope, whether or not intended for medical use. For non-medical applications the single-use coupling described above may be omitted and a more traditional coupling, such as a longitudinal threaded coupling, may be used.

In accordance with one aspect of the present disclosure there is provided apparatus comprising a first device adapted to be releasably operatively coupled to a second device, said second device comprising a detection coil associated with a coupling arrangement of the second device, the first device comprising a sensing coil arranged at a coupling region of the first device, the coupling region being operatively associable with the coupling arrangement of the second device, and a circuit connected to the sensing coil and configured to detect at least coupling of the first device to the second device through interaction of the detection coil with an electrical signal imparted upon the sensing coil.

In accordance with one aspect of the present disclosure there is provided a device, said device being operatively connectable to a medical implement having a closed detection coil located in association with a connecting portion of the implement, said device comprising:

a connection portion by which said device is at least connectable to the implement;

a sensing coil associated with the connection portion such that when the handle and implemented are connected, the sensing coil and the detection coil are magnetically coupled;

an oscillation circuit for which at least said sensing coil forms part of a tuned load thereof;

a detection circuit for detecting a magnitude of oscillation of said oscillation circuit; and an output circuit comprising at least one electrical load operative in response to at least one change in detected magnitude.

In accordance with one aspect of the present disclosure there is provided a medical implement comprising:

a connection portion by which said implement is connectable to a handle device for manipulation;

a closed coil of wire associated with said connection portion and configured to magnetically interact with a coil in the handle to cause the handle to at least emit a signal to the implement.

In accordance with one aspect of the present disclosure there is provided a laryngoscope blade having a coil of wire formed in association with a connection portion to which a laryngoscope handle is operative connectable, the coil being operative to enable operation of lamp configured to emit light from the blade.

Many other aspects are also disclosed.

BRIEF DESCRIPTION OF THE DRAWINGS

At least one embodiment of the present invention will be now be described, by way of example only, with reference to the accompanying drawings, in which:

FIG. 13A shows a side elevation of the laryngoscope handle and FIG. 13B shown an end elevation of the end cap of the handle;

FIG. 14A is a view of the display window of the laryngoscope handle;

FIG. 14B shows the traffic light arrangement of the indicator LEDs;

FIG. 20 is a state variable diagram for general operation of the arrangement of FIG. 19;

FIGS. 29A to 29C show an alternate laryngoscope blade arrangements;

FIG. 30 shows a further laryngoscope blade;

FIGS. 32A and 32B show a still further laryngoscope blade.

DETAILED DESCRIPTION INCLUDING BEST MODE

Laryngoscope System

Figure 1:
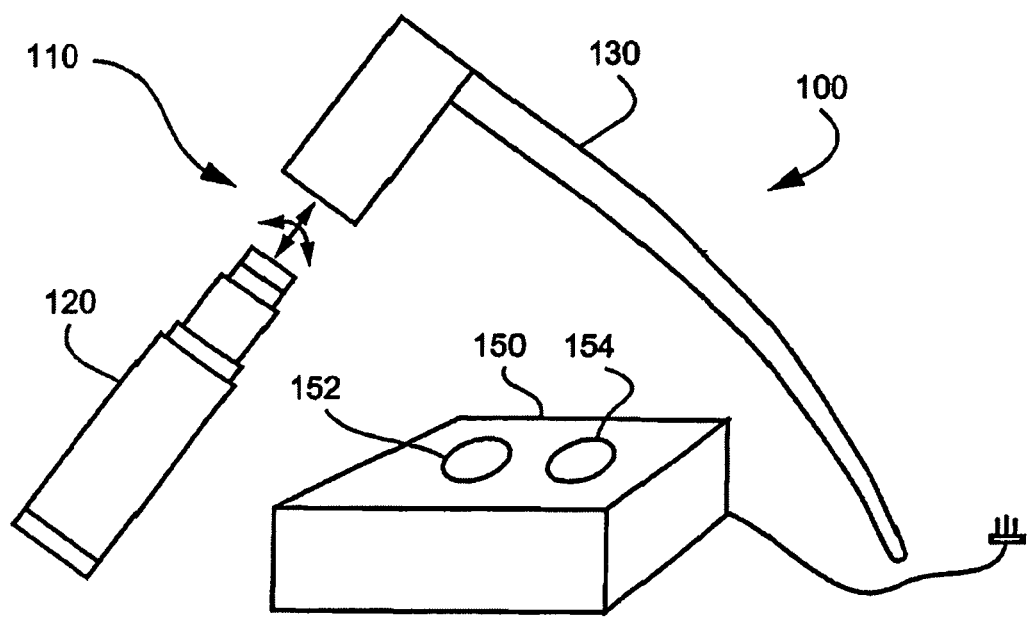
FIG. 1 is a schematic perspective view of a laryngoscope system according to the present disclosure.
Figure 2:
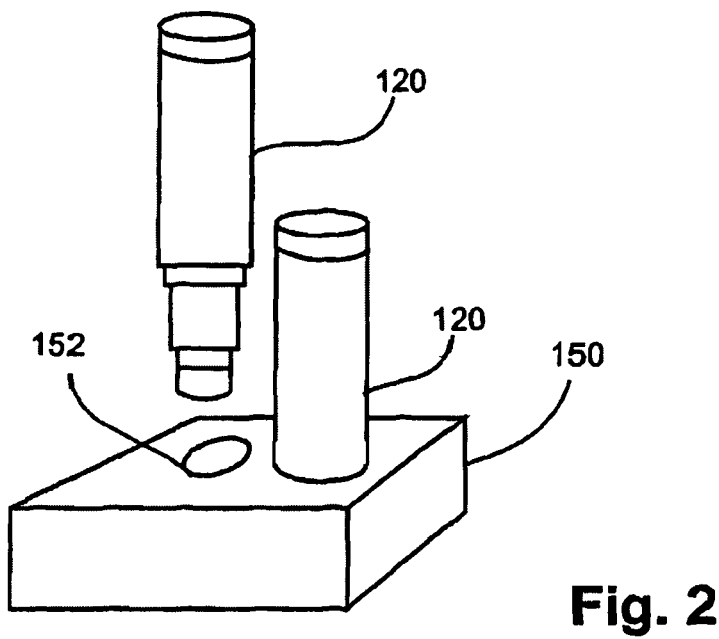
FIG. 2 a schematic view showing how the laryngoscope handle is mounted on the battery charging module.
Figure 3:
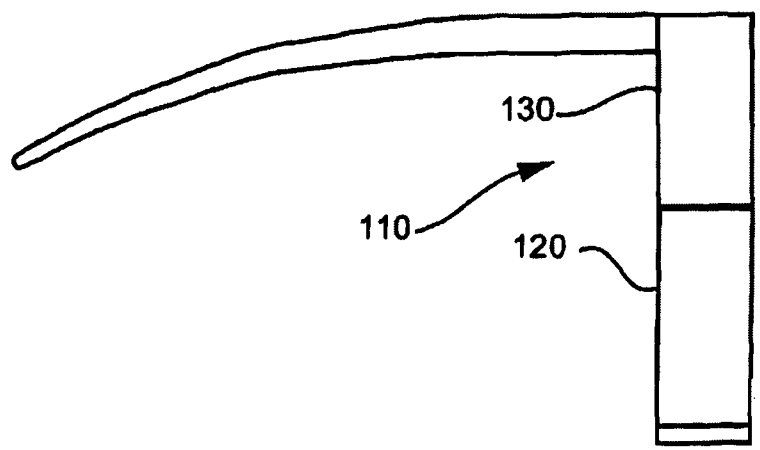
FIG. 3 is a schematic view of the laryngoscope shown in FIG. 1, wherein the laryngoscope blade and handle are connected for use.

FIGS. 1 to 3 show a laryngoscope system 100 incorporating a laryngoscope 110 formed by coupling a reusable handle device 120 to a disposable blade implement 130, as well as a battery charging module 150 for the handle 120. Desirably the system 100 includes two handles 120, permitting at least one handle 120 to be re-charged whilst the other handle 120 is in use coupled to a blade 130.

FIG. 1 shows that the handle 120 is coupled by at least longitudinal insertion into the blade 130, and also rotation about the longitudinal axis of the handle 120 to provide for a snap-fit engagement there between to give the operative configuration illustrated in FIG. 3. The snap-fit engagement is desirably one that is broken by further rotation about the longitudinal axis of the handle 120. The further rotation may be a counter-rotation or one in the same direction that formed the coupling between the handle 120 and blade 130. The further rotation desirably makes unusable coupling components within the blade 130, preventing re-coupling of the handle 120 to the used blade 130, requiring that the used blade 130 be discarded whilst permitting the handle 120 to repeatedly used with a new blade 130 on each occasion. As such this affords a single-use configuration of the blade 130 which is desirable to avoid cross infection between patients.

FIG. 2 shows that one or two of the handles 120 are insertable into respective receptacles 152 and 154 of the charger module 150 for recharging and storage when not in use. The receptacles are shaped to receive by simple insertion a coupling region 123 (seen in FIG. 4) of the handle 120. The handles 120 rest in the receptacles under gravity and may be readily inserted and removed without any need for a locking or clasping engagement.

Laryngoscope Blade

Figure 4:
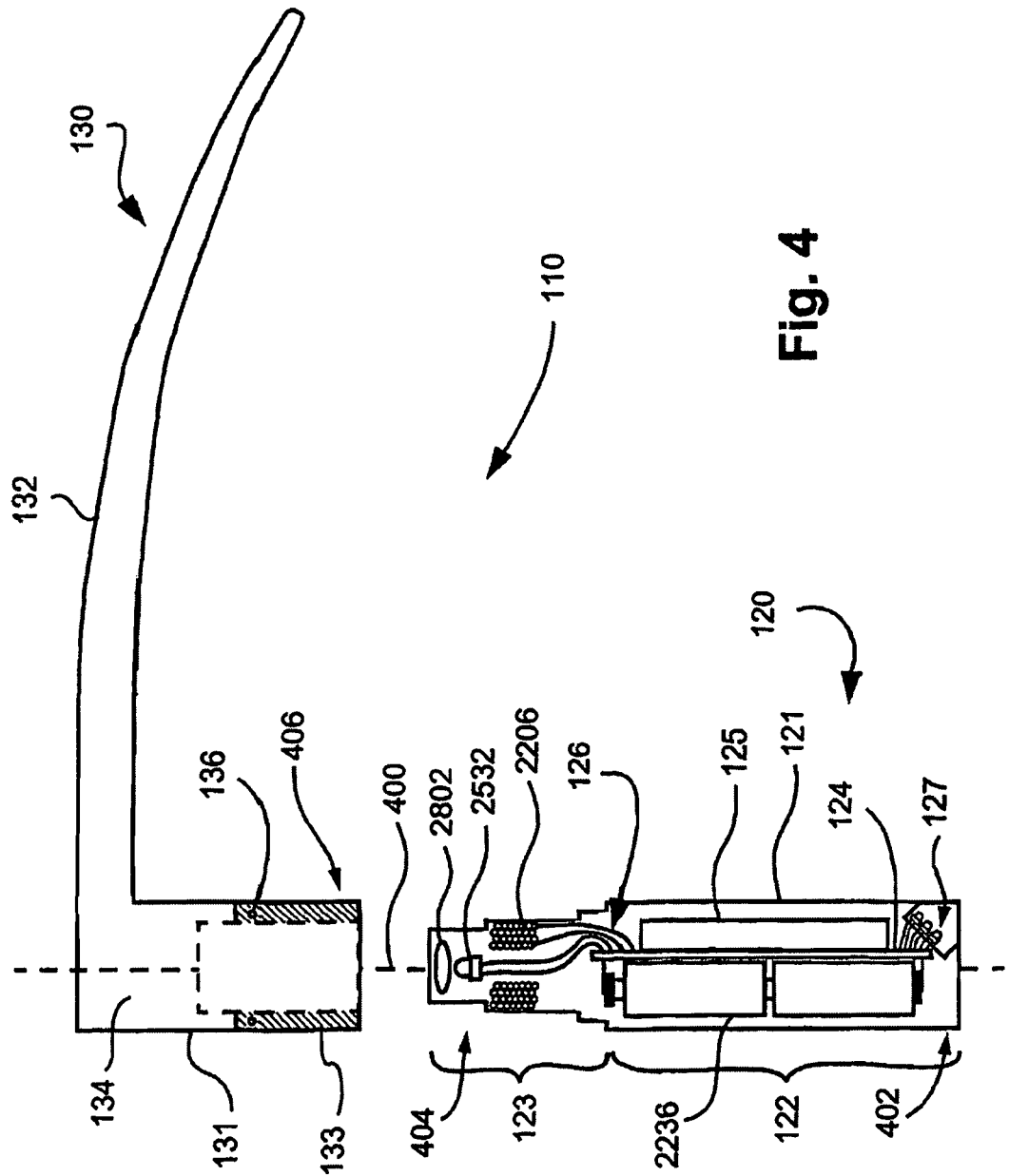
FIG. 4 is an exploded sectional view of the laryngoscope of FIGS. 1-3.

FIG. 4 shows one form of the blade 130 in greater detail. The blade 130 is seen to include a generally arcuate shaped extension 132 for facilitating insertion into the throat of a patient. The extension 132 is unitarily or integrally formed with a cylindrical barrel 131 which is arranged at approximately right-angles to the extension 132. The blade 130 may be formed with an internal light pipe 134 of the kind disclosed in European Patent Publication No. EP 1433413 A2 which extends from a cylindrical proximal end 406 in the barrel 131 to at least within the extension 132. The blade 130 is preferably manufactured of moulded plastics material which may be both conductive and dispersive of electromagnetic radiation such as light. The light pipe 134 is preferably initially reflective to efficiently transmit light directed into the pipe 134 to the extension 132 whereupon the light is emitted through dispersion into the throat of the patient.

The blade 130 includes a generally cylindrical tubular coupling arrangement 133 configured in the proximal end 406 of the barrel 131 to facilitate connection of the blade 130 to the handle 120 through inter-engagement between the coupling arrangement 133 and a coupling region 123 of the handle 120 (discussed below) in the manner described above.

The blade 130 also includes a self-terminated closed coil of wire 136, which may be formed or located adjacent the pipe 134, the function of which is to be described. Desirably, the coil 136, which may be termed a detection coil, and can have between 1 turn (as illustrated in FIG. 4) and about 150 turns and is preferably formed as part of the coupling arrangement 133, the latter being insertable into a complementary cavity moulded as part of the proximal end 406 of the barrel 131.

Laryngoscope Handle

Still referring to FIG. 4, the handle 120 is generally cylindrical and elongate to define a longitudinal axis 400, as discussed above, a proximal end 402 and a distal end 404. The handle 120 is formed by a casing 121 which is stepped radially inwardly near the distal end 404 to define a circumferential annular coupling region 123, and a cylindrical body region 122, extending to the proximal end 402.

The handle 120 is hollow and includes an internal mounting frame (not illustrated) to retain electronic circuitry 125 mounted on one side of a printed circuit board (PCB) 124. An opposite side of the PCB 124 retains batteries 2236. The PCB 124 couples to an indicator arrangement 127 and, via connections 126, to each of a sense coil 2206 and a lamp 2532. The lamp 2532 is preferably formed by a high intensity white-coloured light emitting diode (LED). A lens 2802 is arranged at the distal end 404 to focus light emitted by the lamp 2532 into the light pipe 134 when the handle 120 is coupled to the blade 130. The coil 2206 is positioned within the coupling region 123 and is operative, when the handle 120 and blade 130 are connected, to be closely magnetically coupled with the coil 136 so as to sense the connection and desirably excessive physical pressure being applied to the blade 130, as will be described. The detection coil 136 is preferably positioned within the blade 130 to be substantially co-axially arranged and substantially co-planar with the sensing coil 2206, when the handle 120 and blade 130 are coupled, to provide for near maximum electromagnetic coupling, as will be appreciated from FIGS. 3 and 4.

The Charger Module

Figure 5:
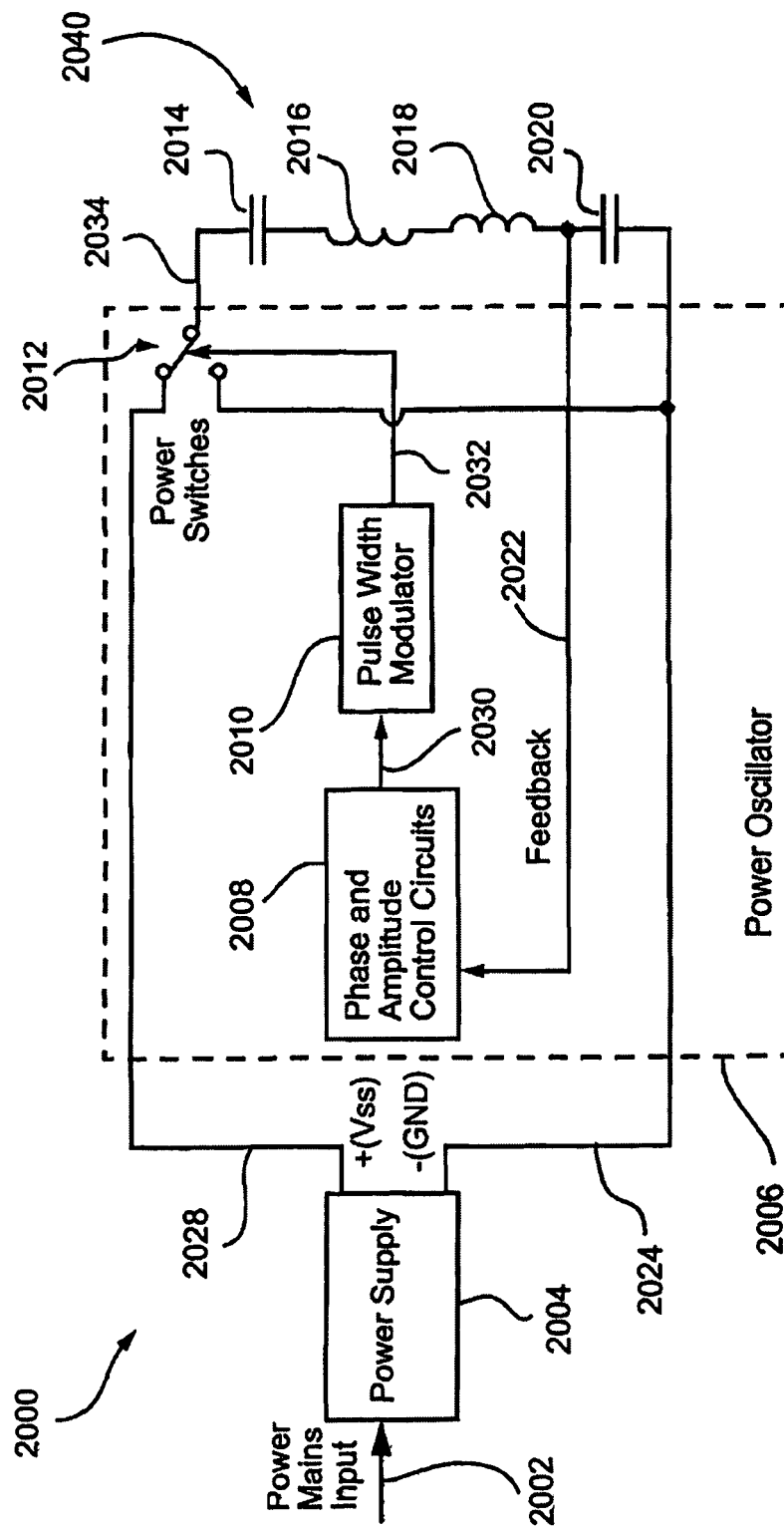
FIG. 5 shows a schematic block diagram representation of a circuit of the charging module.

FIG. 5 shows a schematic block diagram representation of a circuit 2000 of the charger module 150, seen in FIGS. 1 and 2. The circuit 2000 derives power from a mains input 2002 which couples to a power supply 2004 that provides a positive supply 2028 and negative supply 2024 which are able to be selectively coupled to a tuned circuit 2040 via an arrangement of power switches 2012.

The power switches 2012 form part of a power oscillator 2006 incorporating phase and amplitude control circuits 2008 which output a control signal 2030 to a pulse width modulator 2010 which provides a control output 2032 to the power switches 2012. The power switches 2012 operate to alternately connect the tuned circuit 2040 to either the positive supply 2028 or the negative supply 2024. The tuned circuit 2040 incorporates a series arrangement of a first timing capacitor 2014, a first coil 2016, a second coil 2018 and a second tuning capacitor 2020, as illustrated. In an alternate configuration, only one of the capacitors 2014 and 2020 need be used (of one half the capacitance value). A feedback sample signal 2022 is derived from a connection between the second coil 2018 and the second tuning capacitor 2020 and provides a feedback control to the phase and amplitude control circuits 2008.

As can be seen from FIGS. 1 and 2, the charging module 150 includes two receptacles 152 and 154 and is thus able to receive two of the laryngoscope handles 120, one into each receptacle as depicted in FIG. 2. As a consequence, the charging module 150 is able to charge none, one, or two of the handles at any time, and thus must be operable in order to accommodate these variations. In this regard, each of the coils 2016 and 2018 form respective primary windings of respective air core split transformers corresponding to each receptacle 152 and 154. The other part of each split transformer is formed by the coil 2206 of the corresponding idle 120 when inserted into the corresponding receptacle. The coils 2016 and 2018 are connected in series and oppositively poled so that magnetic fields between the coils 2016 and 2018 tend to cancel, which aids in minimizing interference with other devices, such being important in medical environments.

The feedback signal 2022, which monitors the voltage across the capacitor 2020, in turn monitors the current through the coils 2016, 2018 of the tuned circuit 2040 and allows for the pulse width modulator 2010 to adapt the supply based upon the number of handles 120 inserted into the charging module 150.

The charging circuit 2000 preferably operates at about 27.5 kHz, this frequency being chosen empirically to satisfy varying requirements including coil power losses at higher frequencies (skin effect), switching losses, adequate coupling to the handle coil 2206, and sensing operation of the handle 120 (to be described). The circuit 2000 operates by keeping the current in the coil 2016 and 2018 approximately constant by sensing the feedback voltage 2022. When loaded by one or two handles being charged, the voltage 2022 remains the same, but the additional loading increases the resonant frequency by a small amount. The circuit 200 acts like a current source providing the charging current, in which the battery in the handle accepts what charging current is available. This varies with whether one or two handles are present, and the power need by the control circuits within the handles 120 (to be described). Half wave rectification is used for the charging current, so that a flat battery (ie. 0 volts) will not prevent an auxiliary voltage (to be described) being derived from the other half cycle.

Figure 6:
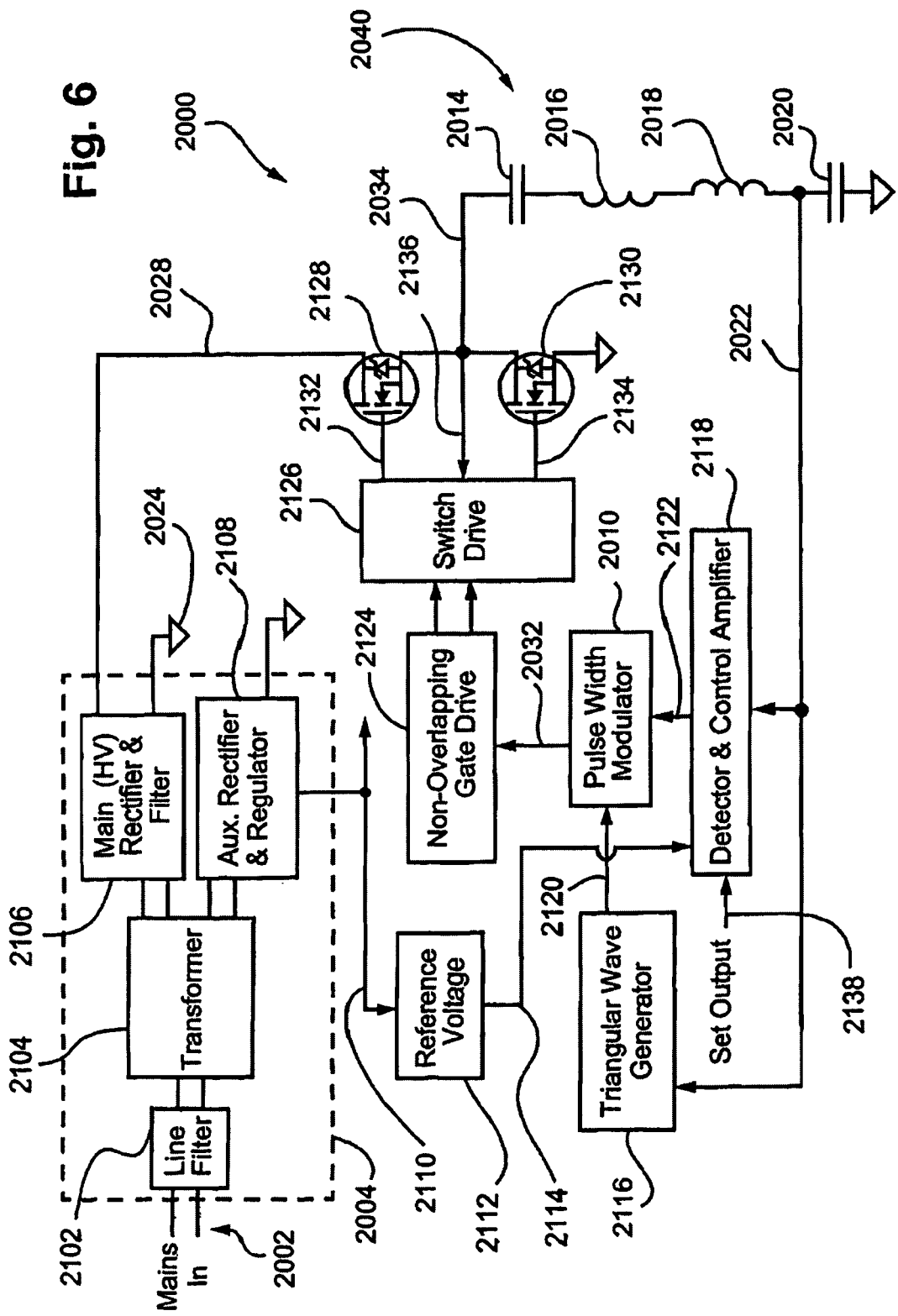
FIG. 6 shows a more detailed schematic representation of the charging module circuit.

FIG. 6 shows a more detailed schematic representation of the charging module circuit 2000. As can be seen, the mains input 2002 supplies a line filter 2012 prior to inputting the mains voltage to a transformer 2104. The line fit 2012 prevents interfering signals from the charger being imposed onto the mains input 2002 and absorbs transients on the mains input 2002 to prevent damage to the charger. The transformer 2104 has two secondary windings, one of which supplies a main rectifier and filter arrangement 2106 to provide a relatively high voltage (approximately 60 volts DC) to a high voltage output 2028 and to an earth connection 2024. The secondary output of the transformer 2104 provides a lower voltage to an auxiliary rectifier and regulator 2108 which provides an output 2110 that supplies a relatively low voltage (eg. about 10 volts DC) to electronic circuits which form the power oscillator 2006 and the remaining components of the circuit 2000. The connections of the output 2110 to most of the circuits shown in FIG. 6 are omitted for the sake of clarity. Notably, the low voltage supply 2110 inputs to a reference voltage regulator 2112 which outputs a reference voltage 2114 as an input to a detector and control amplifier 2118. The triangular wave generator 2116 receives the feedback control signal 2022 from the tuned circuit 2040 and uses the reference voltage 2212 and provides a triangular wave output 2120. The triangular wave 2120 is provided to an input of the pulse width modulator 2010. A further input of the pulse width modulator 2010 is derived from the detector and control amplifier 2118 whose input is supplied from the feedback signal 2022.

The detector and control amplifier 2118 incorporates an envelope type detector arrangement for the feedback signal which provides for the setting of the voltage output of the power oscillator 2006 via a set control 2132 to the circuit 2118. This is used to adjust the sensitivity of the pulse width modulator 2010 to the triangular wave 2120. A pulse width modulated signal 2032 is thereby formed and provided to a non-overlapping gate drive circuit 2124 which creates a pair of outputs to a switch drive circuit 2126, the latter having dual outputs 2132 and 2134 that supply respective gate inputs to MOSFET switches 2128 and 2130 respectively. The non-overlapping gate drive circuit 2124 ensures that neither of the MOSFET switches 2128 and 2130 is turned ON at the same time thereby avoiding overloading of the high voltage supply 2028 and to avoid damaging the switches 2128 and 2130. A local feedback from the output 2034 to the switch drive 2126 is afforded for push-pull operation of the MOSFET switches 2128.

The circuit 2006 operates as a "linear" oscillator controlled by the resonant frequency of the tuned circuit 2040. The illustrated circuit arrangement starts naturally by ensuring that oscillations will build up according to elementary oscillator theory, by ensuring positive feedback is effectively continuous and by a large loop gain. Once oscillations start, magnitude feedback (via 2118) stabilizes the level. The feedback voltage 2022 is filtered by the control amplifier 2118 to reduce ripple sufficient to maintain PWM operation and to control phase shift for stability.

With the arrangement illustrated, when no handles are inserted into the charger module 150, the feedback signal 2022 will be relatively high therefore reducing the width of the pulses output from the modulator 2010 and thus the drive to the MOSFET switches 2128 and 2130. As the load upon the tuned circuit 2040 increases, through insertion of one or more handles 120, and those handles requiring maximum charge, the feedback circuit thus increases the drive to the MOSFET switches 2128, 2130.

The Handle Circuit

Figure 7:
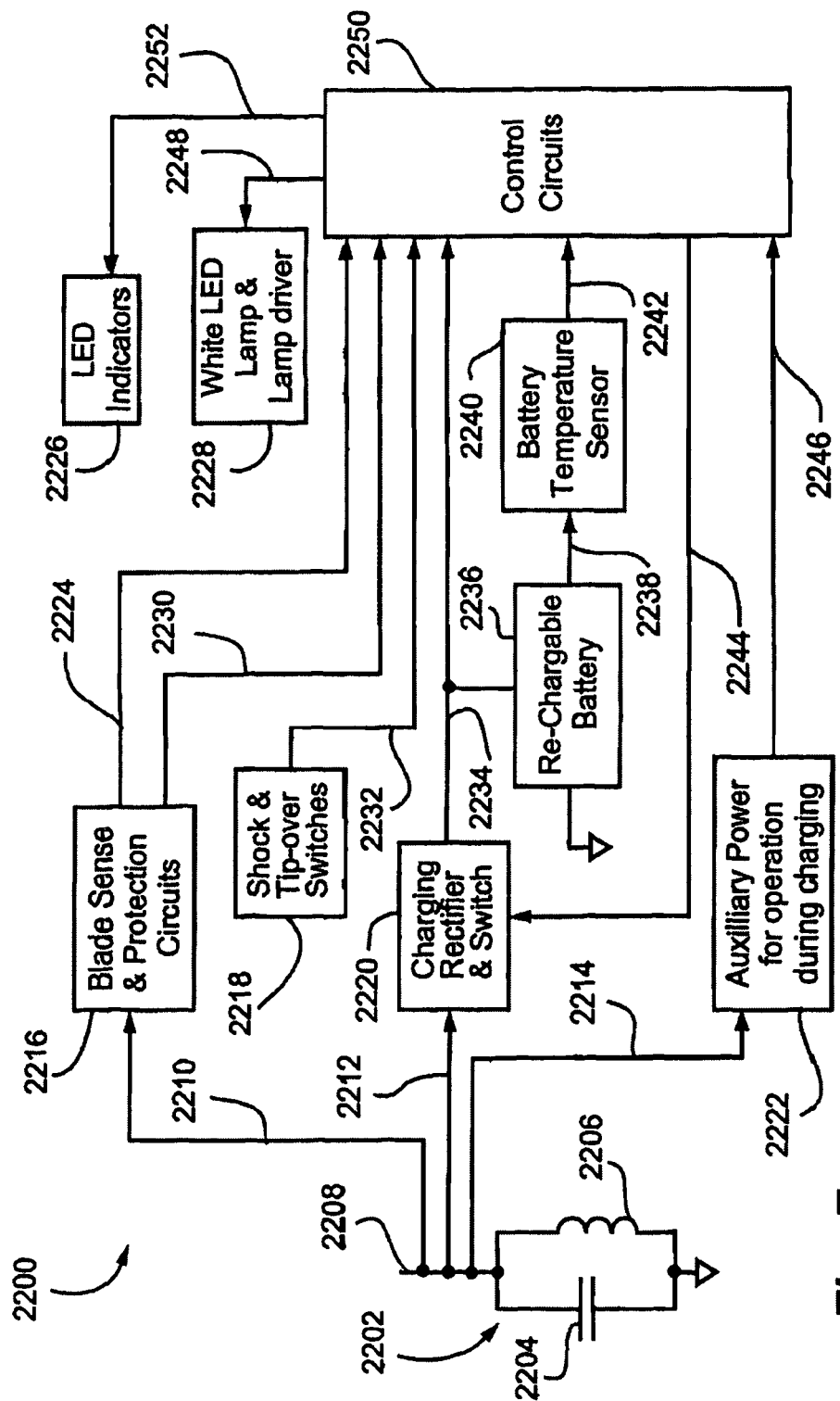
FIG. 7 shows a schematic block diagram representation of a circuit incorporated into the laryngoscope handle.

FIG. 7 shows a schematic block diagram representation of a circuit 2200 incorporated into each of the handles 120 to provide for electronic operation of the laryngoscope 110. As seen from FIG. 7, the circuit 2200 includes a tuned circuit 2202 incorporating a parallel arrangement of a tuning capacitor 2204 and the coil 2206, mentioned above in the description of FIG. 4. The tuned circuit 2202 in the preferred implementation is tuned to a frequency of about 40 kHz, mainly to optimise the force sensor circuit, to be described, and not the charger frequency. When charging, the tuning capacitor 2204 increases the charging current since the capacitor 2204 charges on the negative half-cycle, and discharges on the positive half cycle when current flows into the battery 2236

The tuned circuit 2202 provides an output 2208 that represents a common output to each of three parts of the circuit 2200. Those include an output 2214 to an auxiliary power circuit 2222 for operation during charging, an output 2212 that supplies a charging rectifier and switch 2220, and an output 2210 which provides blade sense and protection circuits 2216.

The various components of the circuit 2200 ultimately provide for the recharging of a rechargeable battery 2236 and the management of operation of the white LED and lamp driver 2228 used to illuminate the white LED 2532, and a number of LED indicators 2226. Control of the LEDs comes via a control circuit 2250.

Initially, upon insertion of a handle 120 into the charging module 150, the tuned circuit 2202 responds to an electromotive force induced from the coils 2016, 2018 and initially energises the auxiliary power circuits 2222 which provide a supply voltage 2246 for consumption during recharging operations of the rechargeable battery 2236. This consumption includes the generation of control signals that are provided via an output 2244 of the control circuits 2250 to activate the charging rectifier and switch 2220 to provide an output voltage 2234 to the rechargeable battery 2236. The rechargeable battery 2236 has a thermal output 2238 which inputs a battery temperature sensor 2240 that forms a temperature control signal 2242 to the control circuits 2250.

An arrangement of shock and tip-over switches 2218 provide inputs to the control circuits 2250 for the operation of the LED lamp 2532 in both a low power "torch" mode when the handle 120 is used alone, and also in a high power laryngoscope mode when the handle 120 is coupled to the blade 130.

The blade sense and protection circuits 2216 are operative to firstly to prevent high voltages present during charging (>30 V peak) from damaging the sense circuits. Also, these circuits operate to sense coupling of the handle 120 to the blade 130 and also to sense a deflection upon the blade 130 during use. The deflection is sensed via the tuned circuit 2202 and is operative to operate an alarm signal via the LED indicators 2252 so as to induce a response from a user of the laryngoscope 110. The circuits 2216 also prevent the charging circuits of the handle 120 from loading the coil 2206 when the handle 120 is not inserted in the charger 150.

Handle Power Supply and Charging

Figure 8:
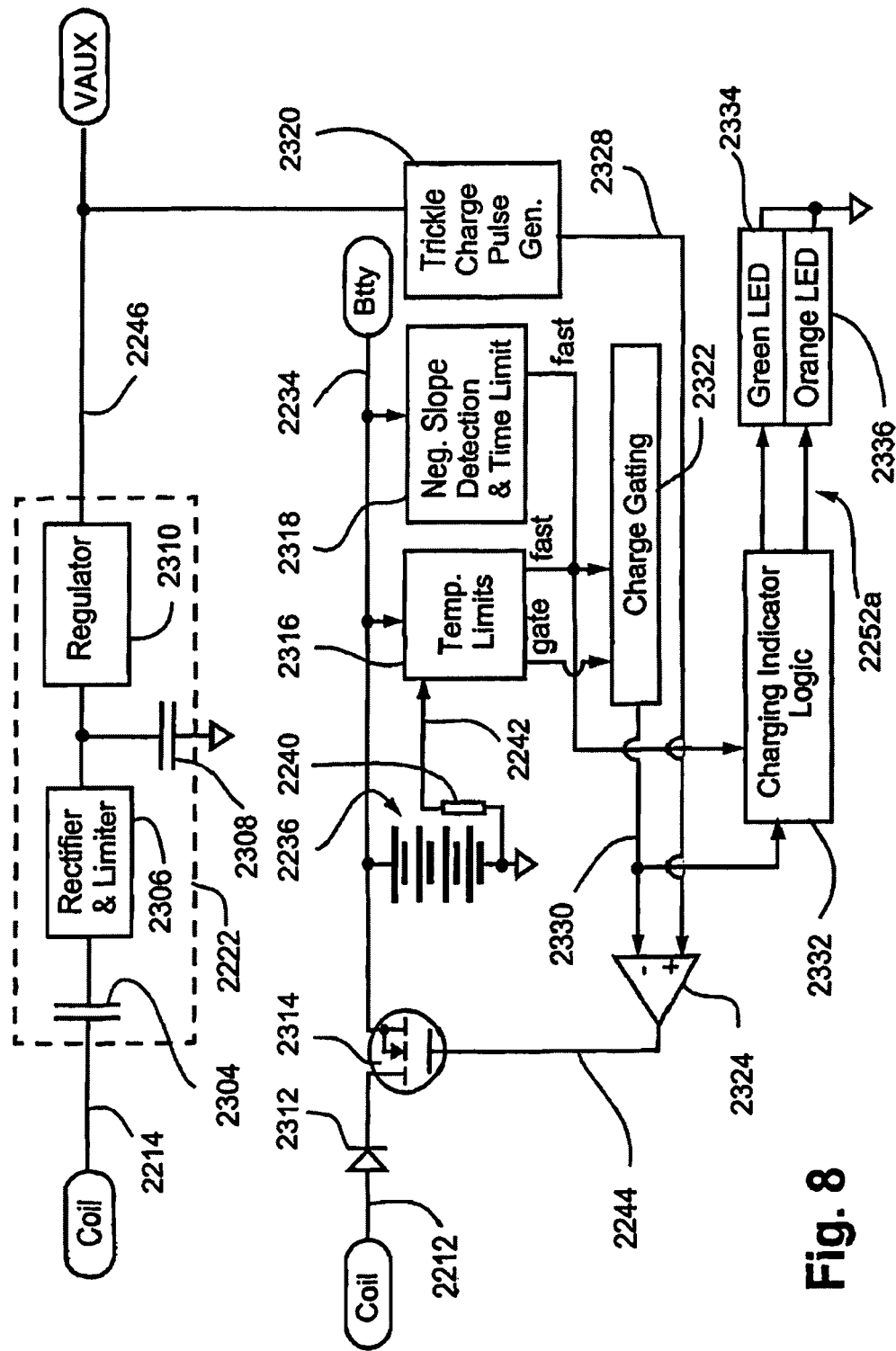
FIG. 8 shows a more detailed schematic representation of a charging part of the circuit of FIG. 7.

Turning now to FIG. 8, it is seen that the first output 2214 from the tuned circuit 2202 supplies the auxiliary power module 2222 via an isolating capacitor 2304. The voltage received from the coil 2206 is provided to a rectifier and limiter 2306 which provides a voltage limited supply to a smoothing capacitor 2308 and to a voltage regulator 2310, an output of which 2246 provides an auxiliary voltage 2246 for the circuit 2200. Accordingly, the auxiliary voltage 2246 will only be enabled when the handle 120 is inserted into the charging module 150 and a charging signal is being received via the air cored split transformer formed thereby. The auxiliary voltage 2246 as seen in FIG. 8 supplies an auxiliary voltage to each of the circuits indicated in the lower portion of FIG. 8 for operation for charging of the battery 2236. Not all connections are shown illustrated for the sake of clarity. A first connection, as illustrated, is to a trickle charge pulse generator 2320 which provides a series of pulses to a comparator 2324 which in turn provides the output 2244 to the gate of a switching MOSFET 2314. When the MOSFET 2314 is turned ON, conduction is permitted from the coil output 2212 via a rectifier diode 2312 to the battery supply line 2234. Accordingly, where the voltage output from the coil is positive relative to the circuit and exceeds the battery voltage, charging current will then flow into the battery 2236.

The battery 2236 is preferably formed by a series connection of four Nickel metal hydride (NiMH) cells and which collectively provide an 800 milliamp-hour storage capacity. This can afford up to about 8 hours of blade lamp use and a nominal 4 hour "quick" charge. A temperature transducer 2240 (eg. thermistor, IC type temperature sensor, thermocouple) is mounted in thermal contact with the case of one of the NiMH cells and thereby adapted to detect the temperature of the battery cells 2236. The transducer 2240 provides a temperature output 2242 to a temperature limit circuit 2316 operable to modulate the switching of the comparator 2324 when high temperatures are sensed on the batteries 2236 during charging operations. In an exemplary circuit, the end of charge voltage on the battery line 2234 was 6.1 volts, giving 5.4 volts nominal operating voltage and about 4 volts as a "discharged" value.

The battery charging circuit of FIG. 8 also includes a negative slope detection and time limit circuit 2318 which is powered via the auxiliary voltage 2246 (not illustrated for clarity) and which senses the battery voltage 2234 to provide a fast charge control signal to a charge gating circuit 2322. The charge gating circuit 2322, together with a gate output of the temperature limit circuit 2316, provides a gating signal 2330 to an inverting input of the comparator 2324 to control operation of the MOSFET switch 2314.

The circuits 2316 and 2318 are preferably implemented using a battery first charge controller such as an MC33340 device and appropriately configured provide for the fast charging of the battery 2236 when the sensed battery voltage is low, and for the trickle charging of the battery when temperature limits are exceeded or the voltage on the battery reaches its desired, nominal level. The control signals generated by the charging control circuits are provided to a charge indicating logic circuit 2332 which provides two outputs 2252a, one each coupling to a green LED 2334 and an orange LED 2336. During fast charge operations, the orange LED 2336 is illuminate and when the charging circuits switch to a trickle charge mode, the orange LED 2336 is extinguished and the green LED 2334 is illuminated.

Blade Sense and Protection

Figure 9:
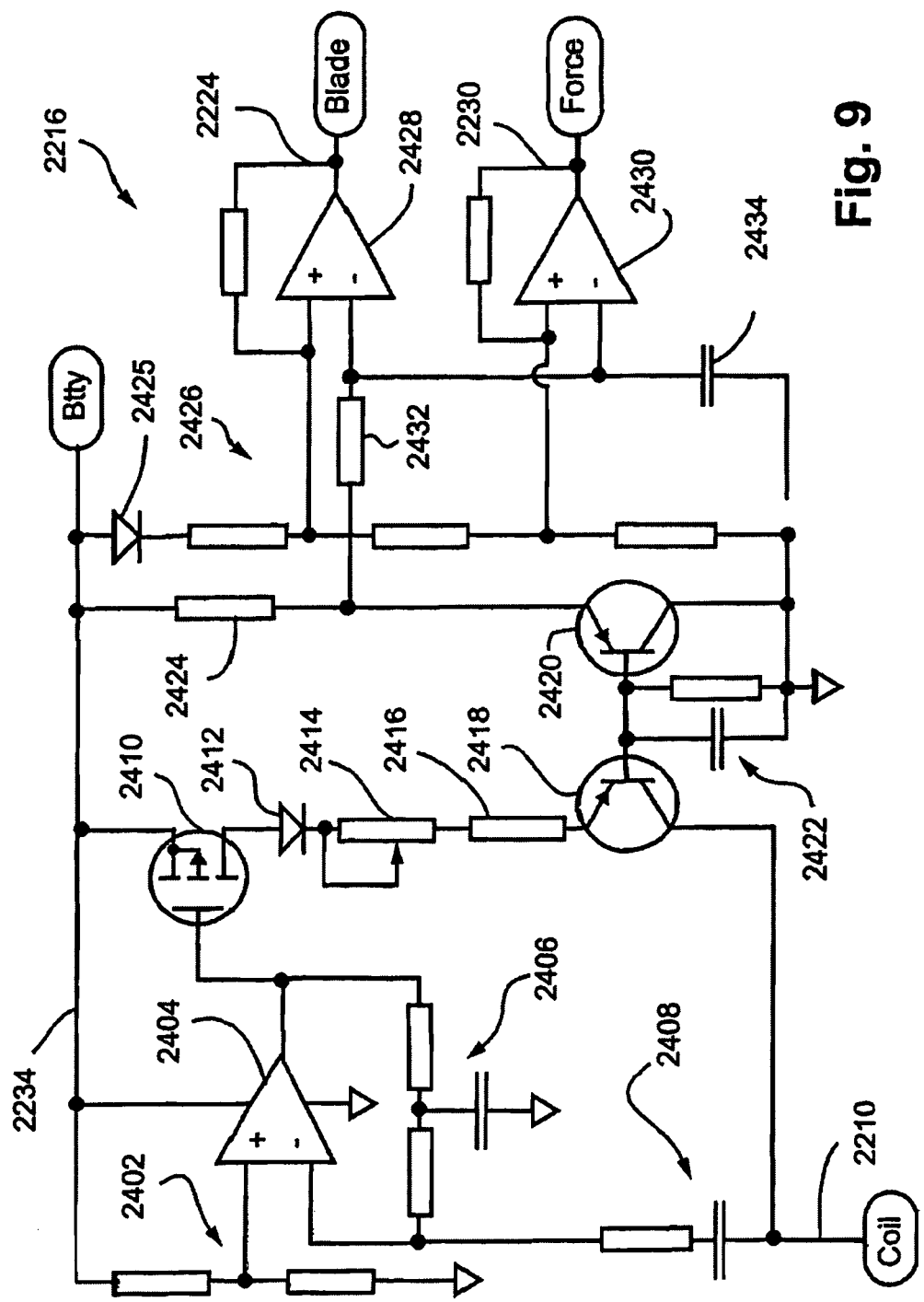
FIG. 9 shows a detailed schematic diagram of the blade sense and protection circuits of FIG. 7.

FIG. 9 shows a detailed schematic diagram of the blade sense and protection circuits 2216 of FIG. 7. The circuits 2216 are operative when se handle 120 is coupled to the blade 130 during laryngoscope operation. As will be appreciated from the above, during such operations, no battery charging voltage is supplied to the tuned circuit 2202, but rather the tuned circuit 2202 forms a load coupled to the connection 2210 representing an output of a feedback oscillator formed by the circuit of FIG. 9. In this regard, FIG. 9 shows a comparator 2404 whose non-inverting input is supplied by a voltage divider 2402 which divides the battery voltage 2234 in half and thus forms a reference voltage for oscillations. A T-network 2406 formed of two resistors and a capacitor provides for tuned local feedback around the comparator 2404 to its inverting input to drive the comparator 2404 into oscillation. The output of a comparator 2404 provides a square wave to the gate of a MOSFET transistor switch 2410 which is thereby selectively enabled to apply the battery voltage via an isolating diode 2412 to a series resistor network formed of a variable resistor 2414 and a fixed resistor 2416 to supply the emitter of a PNP transistor 2418. The collector of the transistor 2418 couples to the tuned circuit 2202 via the connection 2210 and via an RC series network 2404 to the inverting input of the comparator 2404. The base of the transistor 2418 couples to ground via an RC parallel network 2422 and also to the base of a further PNP transistor 2420.

The cumulative effect of this part of the circuit of FIG. 9 is to form an oscillator in which the tuned circuit 2202 forms a part thereof and substantially controls the oscillation frequency of the oscillator. The circuit of FIG. 9 will oscillate when connected to the tuned circuit 2202.

Upon insertion of the handle 120 into the blade 130, the tuned circuit 2202 will interact with the detection coil of wire 136 formed in the coupling arrangement 133. The interaction is due to magnetic coupling between the coils 136 and 2206. The coil 136 provides an additional electromagnetic load upon the handle coil 2206 when the coil 2206 carries an electrical current. The series resistance of the coil 136 may be adjusted, by setting the particular number of turns, to give the desired load reflected into the primary circuit formed using the coil 2206 in the handle 120, to thereby enable the handle 120 to detect, firstly, the presence of the blade 130, and also desirably the amount of force being applied to the blade 130 during use. The interaction is detected in each instance through detecting the loading placed upon the handle coil 2206 by the blade coil 136.

Firstly, for the detection of the presence of the blade 130, only a quantum change in the power consumption caused The detection of that small winding 136 operates to alter the characteristic impedance of the tuned circuit 2202 slightly which in turn adjusts the load formed thereby upon the oscillator circuit of FIG. 9 formed using the comparator 2404. As such, the oscillating signal imparted upon the tuned circuit 2202 loses amplitude as the additional load formed by the coil 136 is increased. The extra load formed by the coil 136 within the blade 130 marginally reduces the parallel resonant impedance of the tuned coil 2206, at a centre frequency of about 40 kHz. However, it is the reduction in amplitude, generally proportional to power, that is detected by the remainder of the circuit 2216.

The handle coil 2206 forms a voltage divider with the effective (resistive) impedance of resistors 2416 and 2414, and a negligible impedance of the MOSFET 2410. The diode 2412 is provided to protect the oscillator during the charging cycle, and its impedance may be ignored during blade sensing operations. The transistor 2418 operates as a self-biased oscillator saturating on the negative peak collector voltage charging the capacitor 2422. The transistor 2420 provides level shifting and temperature compensation to translate the oscillations, and importantly the amplitude of oscillations, to a load resistor 2424. An arrangement of two further comparators 2428 and 2430 is used to derive logic signals from the sensor oscillator. Firstly, a series connection of a resistor divider network 2426 provides a number of reference voltages which are each supplied to the non-inverting inputs of the comparators 2428 and 2430. The network 2426 is supplied via a diode 2425 which compensates for any effect of the protection diode 2412 during sensing operations. A filter circuit formed by a resistor 2432 and capacitor 2434 then provides a filtered voltage to the inverting inputs of each of the comparators 2428 and 2430. The filter operates to covert the frequency of oscillation into a smoother (substantially non-oscillating) voltage signal whose magnitude is substantially proportional to the magnitude of oscillations and the power thereof. The comparator 2428 compares that filtered voltage against a relatively hiker reference voltage to detect the insertion of the handle 120 into the laryngoscope blade 130 to provide a "blade" output 2224, resulting from the coil 2206 interacting directly with the coil 136 formed within the coupling of the blade 130. The fixed coil 136 of blade 130 of FIG. 4 is used to provide only for the detection of coupling between the handle 120 and blade 130.

Where it is desired to additionally detect the force applied to the blade 130 during insertion or other use of the laryngoscope 110, a more elaborate power consumption arrangement is required, ostensibly to detect a greater consumption of power. The circuit 2216 detects this additional consumption using the comparator 2430 which is coupled to a lower reference voltage of the divider 2426 to provide for greater sensitivity to changes in the oscillator voltage as a result of pressure applied to the blade 130. Responses to power consumed in excess of the predetermined magnitude set by the divider 2426 provide a "force" output 2230 from the comparator 2430.

FIGS. 29A-29C show alternate arrangements of a blade 160 configured for both coupling detection and force detection. FIG. 29A shows the blade 160 which is akin to the blade 130 in most respects except as now described. The blade 160 includes a multi-turn coil 136a which is electrically coupled by two leads 162 and 163 to a force switch assembly 161 arranged on an upper outer surface of the blade extension 132. FIG. 29B shows an electrical circuit diagram of the one implementation of the blade 160 in which it is seen the switch assembly 161 is normally open and, when closed, operates to close the circuit formed by the coil 136a, via a resistor 164, thereby changing its impedance and thus the extent of its magnetic coupling with the handle coil 2206. A shunt resistor 168 may be used to regulate the impedance of the coil 136a, as seen by the switch 161, to permit reliable operation and to ensure that operation substantially independent on the winding resistance of the coil 136a. The magnitude of the resistors 164 and 164 may be varied from 0 ohms to about 5K ohms so as to achieve a desired electrical loading effect. Whilst the switch 161 is open, detection of coupling between the blade 160 and the handle 120 is achieved due to a relatively small, but nevertheless detectable, increase in loading due to the load impedance of the coil 136a and resistor 168. When the switch 161 is closed, the resistor 164 further shunts (lowers) the impedance. Typically the resistor 164 has a value lower than that of the resistor 168. For example the resistor 168 may have a value of 5K ohms, whereas the resistor 164 may have a value of 100 ohms. A structure of the switch 161 is shown in FIG. 29C where the switch 161 is formed of a metallised layer 167 bonded to the upper outer surface of the extension 132. An insulating mesh 166 is then sandwiched between the metal layer 167 and a conductive polymer layer 165. The connections 162 and 163 connect to the polymer layer 165 and the metal layer 167 respectively. When not in use, or when no force is applied, the insulating mesh 166 maintains a separation between the layers 165 and 167 to prevent electric connection therebetween. When excessive force is applied, for example by a patient biting down upon the blade 160 during insertion, or by the blade being inappropriately pushed against the wall of the throat, the layer 165 is forced against the mesh 166 so that part s of the layer 165 pass through the mesh 166 and contact the metal layer 167, thereby electrically closing the switch 161. When this occurs, the coil 136a is closed via the resistor 164 and a greater magnetic load is formed which increases the load upon the handle coil 2206.

FIG. 30 shows a further blade 170 where the extension 132 and barrel 131 are manufactured separately and joined, for example by epoxy gluing or ultrasonic welding. In the blade 170, the extension is moulded to form a cylindrical post 172 longitudinally aligned with the coupling 133 and about which a coil 136b may be formed. The coil 136b is used in this arrangement may be used for both coupling and force detection. For coupling detection, in view of its longitudinal positioning and proximity to the location in which the handle coil 2206 resides when inserted, a magnetic coupling is formed that may be detected as before. That coupling establishes a steady state power "consumption" of the air cored transformer arising from the co-placement of the coils 2206 and 136b. When force is applied to the extension 132, relative resilient movement between the extension 132 and barrel 131 results causing small physical displacement of the post 172 as depicted by the two arrows in FIG. 30 adjacent the coil 136b. That small displacement moves the coil 136b away from the longitudinal axis and operates to change the amount of magnetic coupling between the coils 2206 and 136b, thereby changing the load. Typically, that change will be a reduction in the coupling and thus the load. As such, this reduction in load can be detected, using circuitry similar to that shown in FIG. 9, which operates to detect an increase in load for "force". Significantly, in this configuration, a flexing of the resilient mechanical join between the barrel 131 (and thus the handle 120) and the extension 132 changes the magnetic coupling sufficient for force detection.

FIG. 32A shows a further blade 180 also having a post 172 depending from the extension 132. In this configuration, two mechanical contact switches 182 and 184 are arranged within the barrel 131 adjacent the post 172 and wired in parallel to a circuit incorporating the winding 136a. This configuration therefore represents something of a combination of FIGS. 29 and 30. In FIG. 32A again due to the resilient coupling between the barrel 131 and extension 132, the post 172 moves when excessive force is applied to the blade 180. When that movement is sufficiently great, the post will engage one of the contact switches 182, 184 which then operates as be before to alter the loading on the magnetic coupling between the handle 120 and the blade 180. An electrical circuit of this configuration is shown in FIG. 32B where the switches 182 and 184 are parallel connected to each provide the necessary "force" indication through altering the load. Electrical wire connections between the coil 136a, and the switches 182, 184 are not shown in FIG. 32A for the sake of clarity.

Using the blades 130, 16, 170, and 180 affords the ability to form a simple "coupling" detection blade, and further a blade by which the laryngoscope can detect both coupling and excessive force. The latter blade may be most suitable for teaching environments whereas the coupling blade may be less expensive a more suited to use by trained persons and in high volume locations (eg. operating theatres).

Lamp Drivers

Figure 10:
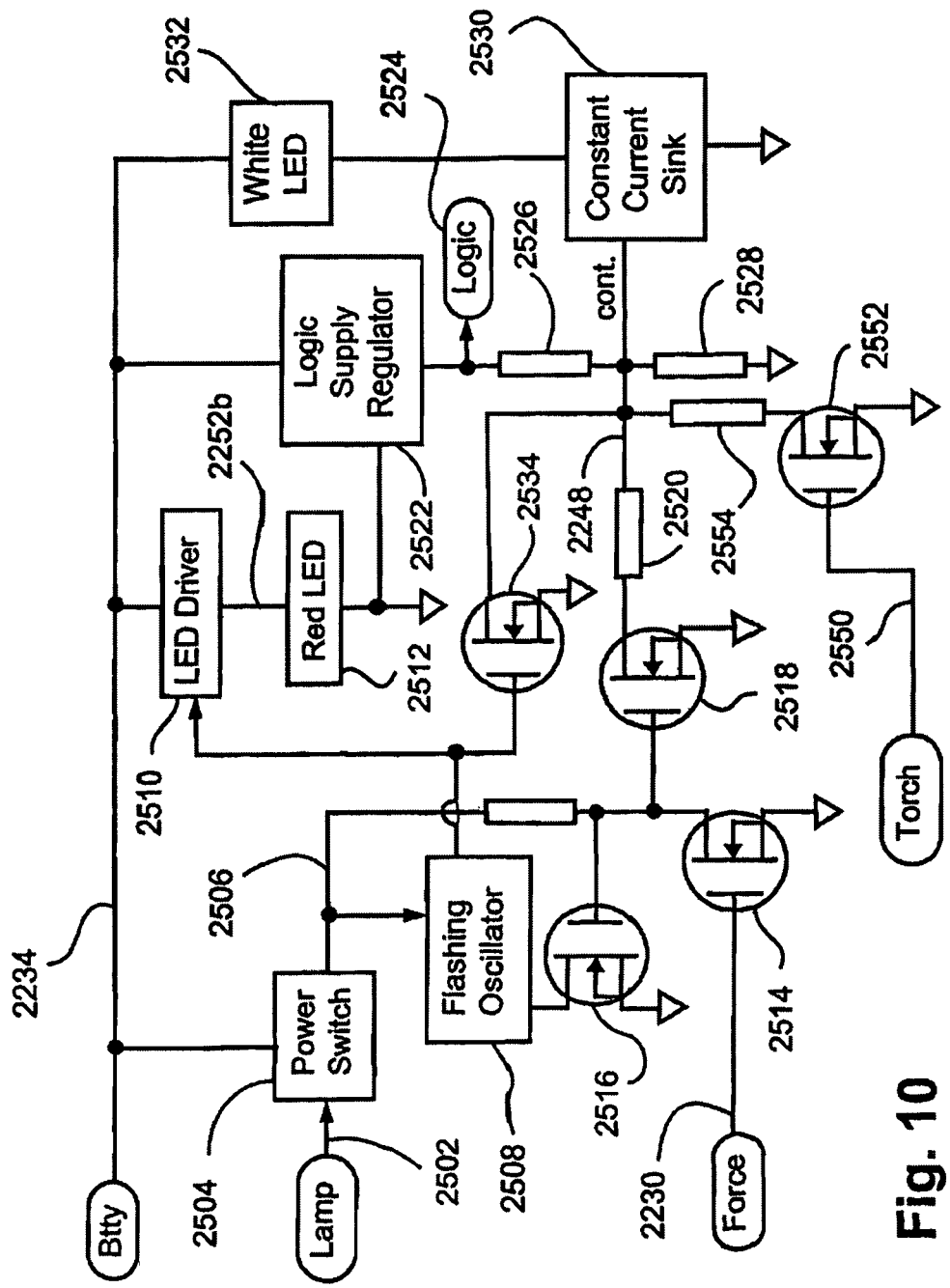
FIG. 10 shows a more detailed schematic of the lamp drivers of FIG. 7.

Turning now to FIG. 10, a "lamp" input 2502 is derived from the control circuits 2250 (described later with reference to FIG. 11) and is used to operate the white LED lamp 2532 forming part of the module 2228 of FIG. 7. The lamp input 2502 is enabled when the blade signal 2224 of FIG. 9 is enabled, and supplies a power switch 2504 which, when the lamp signal 2502 is active, operates to couple the battery voltage 2234 to a power supply line 2506 representing an input to a flashing oscillator 2508. The power supply line 2506 also supplies a voltage to a MOSFET transistor 2514 which receives as its input the force signal 2230 derived from the circuit of FIG. 9. A further MOSFET transistor 2516 detects the voltage on the drain of the transistor 2514 to provide for enablement of the flashing oscillator 2508 for control of its output, which is applied to the gate of a further MOSFET 2534 and to a LED driver circuit 2510. The drain of the MOSFET 2514 also supplies a gate of a further MOSFET 2518 which, together with the MOSFET 2534 combine to form a control signal 2248 representing a control of a constant current sink circuit 2530.

A logic supply regulator 2522 operates from the battery voltage 2234 and supplies a further low voltage regulated supply for operation of the control circuits 2250. Particularly, the logic voltage 2524 supplies a divider circuit formed by resistors 2526 and 2528, the connection between which forms the control signal 2248 for the constant current sink 2530. The constant current sink 2530 provides a current sink for the white LED 2532 for its regulated operation in one of two modes.

In this regard, the handle 120 and in particular the white LED 2532 is operable in either a "torch" (half-power) mode when the handle 120 is decoupled from the blade 130, and also in a laryngoscope (high-power) mode when the handle 120 is coupled to the blade 130. In each case, the lamp signal 2502 is enabled.

When being used in the laryngoscope (high-power) mode, and assuming the force signal 2230 which provides an input in FIG. 10 will be at a logic low level (ie. no excessive force being applied to the blade 130), such will provide for the MOSFET 2514 to be OFF. The effect of this is that the MOSFET 2518 will have its gate raised to relatively high voltage level approaching that of the power supply 2506. This will cause each of the MOSFET's 2516 and 2518 will be tuned ON. The MOSFET 2516 will also turn ON to disable the flashing oscillator 2508 thereby preventing operation of the red LED 2512 via the LED driver 2510. Further, the MOSFET 2518 is connected to influence the control signal 2248 of the constant current sink 2230 via a resistor 2520. As a consequence, when the MOSFET 2518 is turned ON the control signal 2248 is reduced to cause a predetermined current flow via the sink 2530 and thus through the white LED 2532. This results in a high power of the white LED 2532.

When being used in the torch mode, the handle 120 is not coupled to the blade 130 and as a consequence, the blade sense and protection circuits of FIG. 9 are not active to provide either the blade signal 2224 or the force signal 2230. Similarly, the force signal 2230 which provides an input in FIG. 10 will be at a logic low level providing for the MOSFET 2514 to be OFF. The control circuit of FIG. 11 outputs a "torch" signal 2550 which is supplied to the circuit of FIG. 10. The signal 2550 supplied the gate of a further MOSFET 2552 which couples to the current control voltage 2248 via a resistor 2554. When the torch signal 2550 is enabled, the MOSFET 2552 turns ON, in turn drawing more current through the resistor 2526 and thus lowering the control voltage 2248. Appropriate selection of the resistor 2554 will thus cause the control voltage 2248 to drop to a value sufficient to reduce the current drawn by the current sink 2530 and thus reduce the light output of the white LED 2532 to a value approximately half the light output when only the MOSFET 2518 is enabled.

Returning to the high-power laryngoscope mode, a voltage on the force input 2230 also operates to turn on the MOSFET 2514 and turn off the MOSFET 2516 which enables the flashing oscillator 2508. This in turn drives the LED driver 2510 to operate the red LED 2512 to flash ON and OFF and thereby provide a visual warning signal to the user that excessive force is being applied. The MOSFET 2534 will also be activated ON and OFF. Since the drain connection of the MOSFET 2534 connects directly to the control voltage 2248, the MOSFET 2534 turning ON will act to short out the control voltage 2248 to effectively 0 volts, thereby disabling the current sink 2530 and turning OFF the white LED 2532. The operation of the flashing oscillator will thereby modulate the white light output from the white LED 2532 providing a further visual indication of excessive force, perhaps within the throat of the patient. During flashing the peak light output may be varied.

Switch Control

Figure 11:
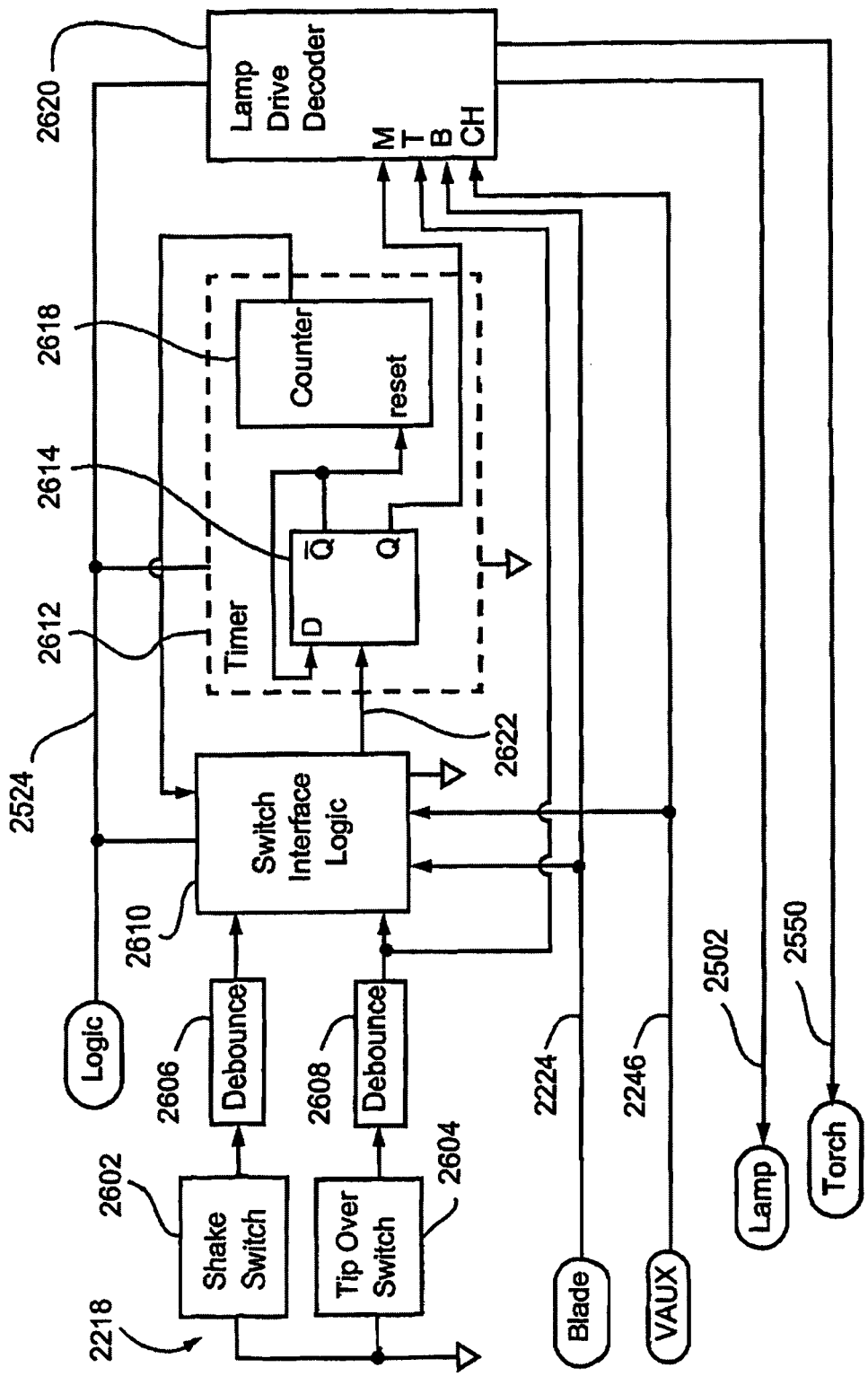
FIG. 11 shows the remainder of the control circuits of FIG. 7.

FIG. 11 shows the remainder of the control circuits 2250 which receive inputs from the shake and tip-overs switches 2218, the blade input 2224, the auxiliary voltage 2246 and which provides the lamp output 2502 and torch output 2550. As seen, a shake switch 2606 provides a switched input to a debounce circuit 2606. The shake switch 2606 is a proprietary device available for example from AssemTech Europe, part of the Comus International Group of Companies. The switch 2606 momentarily makes contact with acceleration in the axial direction, nominally in one sense. The switch 2606 uses a small ball bearing and spring to hold such away from contact and may be considered a crude accelerometer. A tip-over switch 2604, for example formed by a mercury switch, or a dry contact device also available from AssemTech Europe, also provides an input to a corresponding de-bounce circuit 2608. Each of the de-bounce circuits 2606 and 2608 output to a switch interface logic circuit 2610. Further, the output of the tip over de-bounce circuit 2608 provides a tip-over input to a lamp drive decoder 2620.

In operation, the shake and tip-over switches 2218 permit a user of the handle 120 to turn the lamp 2532 on and off, whether or not the handle is connected to the blade 130, by simply shaking the handle 120, lifting the handle 120 from horizontal rest, on a table for example, or by tilting the handle 120 through about 90 degrees. The tilting may be in line with longitudinal axis 400 or a lateral tilt. A lateral tilt may for example occur whilst the blade 130 is emplaced in a patient's throat and the patient's head is rolled to the side, during an operation. Since the switches 2218 are formed on the PCB 124, such are sealed within the casing 121 of the handle 120 and of themselves do not present a contamination risk.

The interface logic 2610 also receives the auxiliary voltage 2246 and blade signal 2224 and outputs a number of signals to a D flip flop 2614 which, together with a counter 2618, forms a timer 2612. The ripple counter 2618 provides a feedback input to the switch interface logic and collectively those devices provide an "M" input to the decoder 2620. The auxiliary voltage 2246 provides a "charge" input to the decoder 2620 and the blade signal 2224 provides a corresponding "blade" input to the decoder 2620. The decoder 2620 is operative firstly to disable operation of the lamp, and thus the lamp signal 2502, during charging operations and further to enable operation of the lamp 2532 during torch operations and when the blade 130 is connected. The decoder 2620 outputs the lamp signal 2502 and the torch signal 2550. Operation of the white LED 2532 is also controlled by virtue of the timer 2612, via the M input, in the fashion to be described with reference to FIG. 12.

Figure 12:
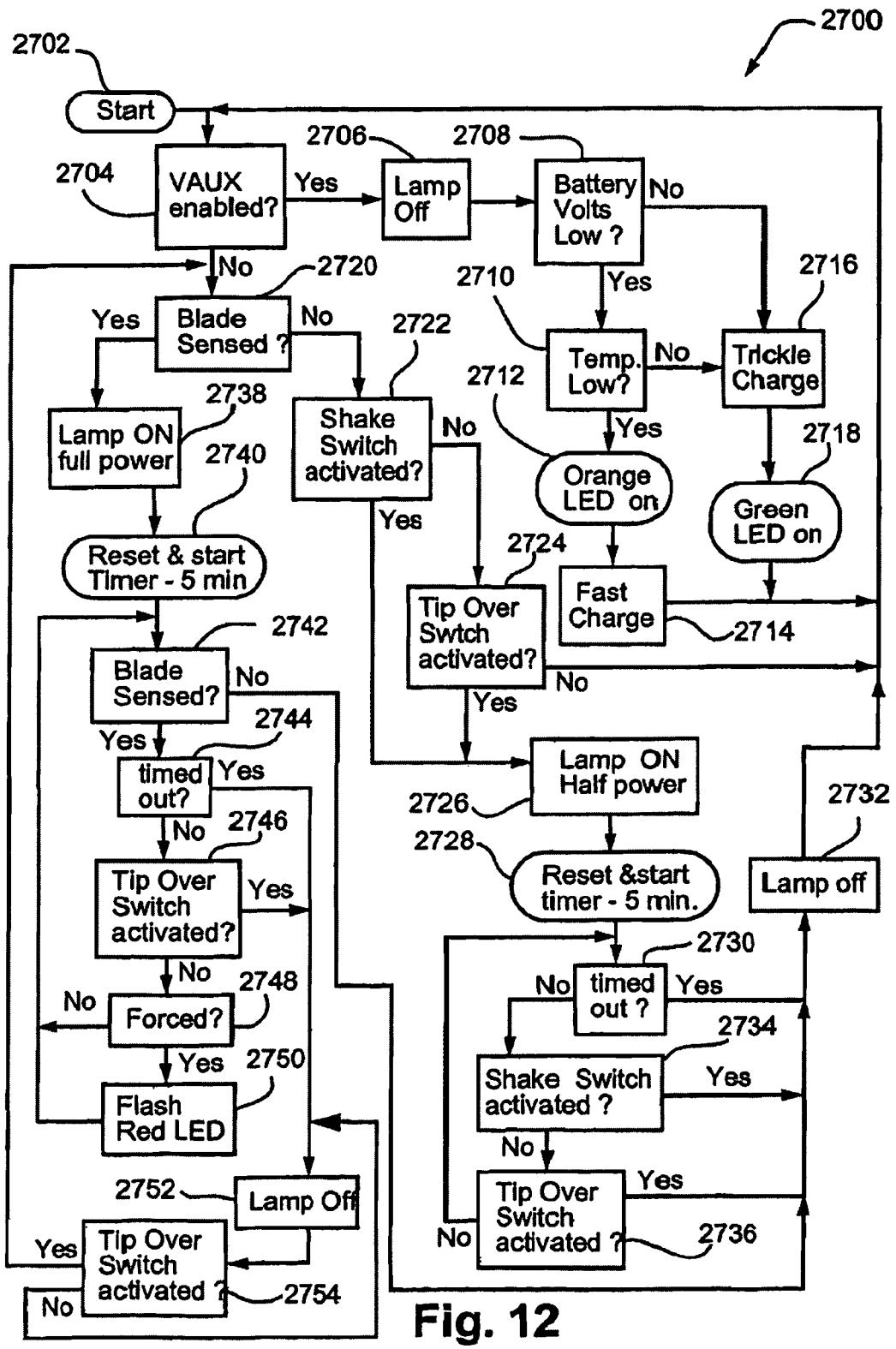
FIG. 12 shows a flowchart of a method of operation of the control circuits to control operation of the handle during charging, and during laryngoscope operations.

FIG. 12 shows a flowchart of a method 2700 of operation of the control circuits 2250 to control operation of the handle 120 during charging, and during laryngoscope operations with the blade 130 connected thereto. The method 2700 particularly illustrates the logic performed by the control circuits of FIG. 11. References to the "lamp" in FIG. 12 and the following description are references to the laryngoscope lamp preferably formed by the white LED 2532.

The method 2700 has a nominal start entry point 2702 useful for consideration. At a first operative step 2704, if the auxiliary voltage 2246 is present, charging operations are clearly intended and step 2706 turns the lamp off and step 2708 checks the battery voltage. If the battery voltage is low, charging will be desired and step 2710 checks if the temperature of the battery 2236 is low. If so, the orange LED 2336 is turned on in step 2712 and the handle 120 enters a fast charge mode 2714 during which time the battery 2236 is charged. Charging continues as long as the auxiliary voltage 2246 is sensed at step 2704. When the battery voltage reaches its appropriate nominal voltage, as sensed in step 2708, the battery charger returns to a trickle charge mode 2716, the orange LED 2336 is extinguished, and the green LED 2334 is turned on in step 2718. Similarly, if a high temperature is detected during charging operations in step 2710, the charger reverts to the trickle charge mode in step 2716.

If, in step 2704, the auxiliary voltage 2246 is not sensed, step 2720 detects whether or not the blade signal 2224 is sensed. If no blade is sensed, such would be equivalent to the handle 120 being held for torch use, or resting, on a table for example. Step 2722 then detects whether or not the shake switch 2602 has been activated. If not, step 2724 detects whether the tip-over switch 2604 has been activated. If not, no further operation takes place. If either of the switches 2602, 2604 have been activated in steps 2722 or step 2724, the lamp (white LED) 2532 is turned on in step 2726 in its half power mode of operation as discussed above with reference to FIG. 10. At that time, the timer 2612 is reset and started to time for a period of 5 minutes. The laryngoscope handle 120 may then be used as a torch, with white light emitted from the LED 2532 through the lens 2802. Step 2730 checks whether or not the timer 2612 has timed out. If so, the lamp 2532 is turned off in step 2732 and control returns to the start 2702. If the timer 2612 has not timed out, step 2734 then tests whether the shake switch 2602 has been activated and step 2736 tests whether or not the tip-over switch 2604 has been activated. If either of those switches 2602, 2604 is activated, the lamp 2532 is again turned off in step 2732. If not, the method 2700 cycles back to step 2730 to determine whether or not the timer 2612 has been timed out. As a consequence, this controls operation of the handle in the torch mode of operation.

Where the blade is sensed at step 2720, the lamp 2532 is turned on full power in step 2738. Step 2740 then follows to reset and start the timer 2612 for a period of 10 minutes. This is equivalent to laryngoscope operations where it may take the physician some time to appropriately position the laryngoscope 110 within the patient. Step 2742 then tests whether or not the blade 130 has been sensed. If the blade 130 has been removed, the lamp is turned off at step 2732. Next, step 2744 tests whether or not the timer 2612 has timed out. If so, the lamp 2532 is turned off at step 2752. Step 2754 then tests whether or not the tip-over switch 2604 has been activated. If so, control then returns to step 2720 where, if the blade 130 is again sensed, the lamp 2532 is then turned on at step 2738 and the method thereby continues. If the tip-over switch has not been activated in step 2754, control returns to step 2752 where the lamp 2532 is kept off. As a consequence of this mode of operation, the laryngoscope may be appropriately positioned within the patient with the lamp tuned on, and remain in the patient, as is sometimes the case during surgery, for an extended period. During that period, the lamp will turn off after five minutes thereby conserving battery power. If at any time it is desired for the lamp to be turned on, the tip over switch need only be activated through tipping over the handle by tilting the head of the patient. Thus the lamp will then be turned on permitting further inspection and/or relocation as required.

If during operation of the 10 minute timer in step 2704, the tip over switch is activated at step 2706, then the lamp is turned off. If not, step 2748 detects whether or not the excessive force is being applied to the blade. If so, step 2750 then flashes the red LED 2512 and the white LED lamp 2532. Control then returns to step 2742 during the operation of the timer.

It will be appreciated from FIG. 12 that the arrangements described in that method can be implemented using microcontroller arrangements. In this regard, the control circuits 2250 of FIG. 7 may be replaced by a suitably programmed microcontroller operative to detect the various inputs from the other circuits shown in FIG. 7 and described above. The microcontroller may be used to implement for example a software version of a battery charging controller in which battery voltage and the battery temperature sensors may be provided to analogue to digital converters, forming part of the microcontroller enabling direct measurement of the battery voltage and battery temperature during charging operations.

FIG. 13A shows an exterior view of the handle 120 which is substantially cylindrical in shape and within which is enclosed the batteries 2236 and the electronic circuits described above. The casing 121 of the handle 120 is closed at the proximal end 402 by an end cap 2802 which includes a display window 2804 which is operatively associated with each of the LED indicators 2226 (2512, 2336, 2334). As seen from FIG. 13A which is a side elevation view and FIG. 13B which is an end elevation view of the end cap 2802, the display window 2804 is shaped to extend around the corner and thus provide multi-directional viewing of the LED indicators 2226.

Detail of the display window 2804 is seen in FIG. 14A where the window may be moulded from substantially transparent plastics material and which incorporates a solid block portion 2904 which extends around the 90 degree angle formed on the edge of the end cap 2804 and which includes a receptacle 2902 for placement of the LED's 2512, 2336, and 2334. The placement of the LED's in the receptacle 2902 is seen in FIG. 14B. In this fashion, the LED indicators 2226 formed by the window 2804 and the arrangement of the red LED 2512, the orange LED 2336 and the green LED 2334 provides for a "traffic-light" unitary arrangement of the indicators 2226 such that each of the red, orange and green visual indications are displayable through the window 2804. Accordingly, the window can provide to the user a clear indication as to the either the charging state of the handle 120 or the over supply of pressure to the blade 130 when being used as a laryngoscope 110. The orange LED 2336 may be substituted by a yellow LED. Further, whilst not shown in the drawings, an audible alarm may be used in place of or in addition to the red LED 2512. One difficulty in implementing an audible alarm is the sealing of the casing significantly reduces the emission of sound, thereby increasing power consumption for useful audio levels. Further, during intubation operations, the proximal end of the handle 120 incorporating the window is immediately in the line of sight of the medical practitioner and therefore the red LED 2512 would be quite visible.

FIG. 13A also illustrates the operative portions of the handle 120 associated at its distal end 404 from the end cap 2804. Notably, the distal end incorporates the lens 2802 arranged to focus light emitting from the white LED 2532 onto the optical device 135 formed within the blade 130. It will be appreciated from FIG. 13A that the white LED 2532 is located within the handle 120 preferably at a focal point of the lens 2802.

Also shown illustrated in FIG. 13A, and in phantom, is the coil 2206 of the tuned circuit 2202 of FIG. 7. This coil 2206 is configured to interact with both the coils 2016/2018 within the charger module 150 and also the coil 136 formed of the re-use prevention coupling arrangement 133 in the blade 130. The handle 120 is a sealed unit incorporating no user physically operable or actuable openings, such as lever switches and the like. In view of the blade 130 being disposable and disengagable from the handle 120, contamination of the handle 120 is not likely to be as severe as traditional laryngoscope handles. Sterilization may be performed by washing, without a need for expensive and possibly damaging autoclaving.

Further Implementation

Figure 19:
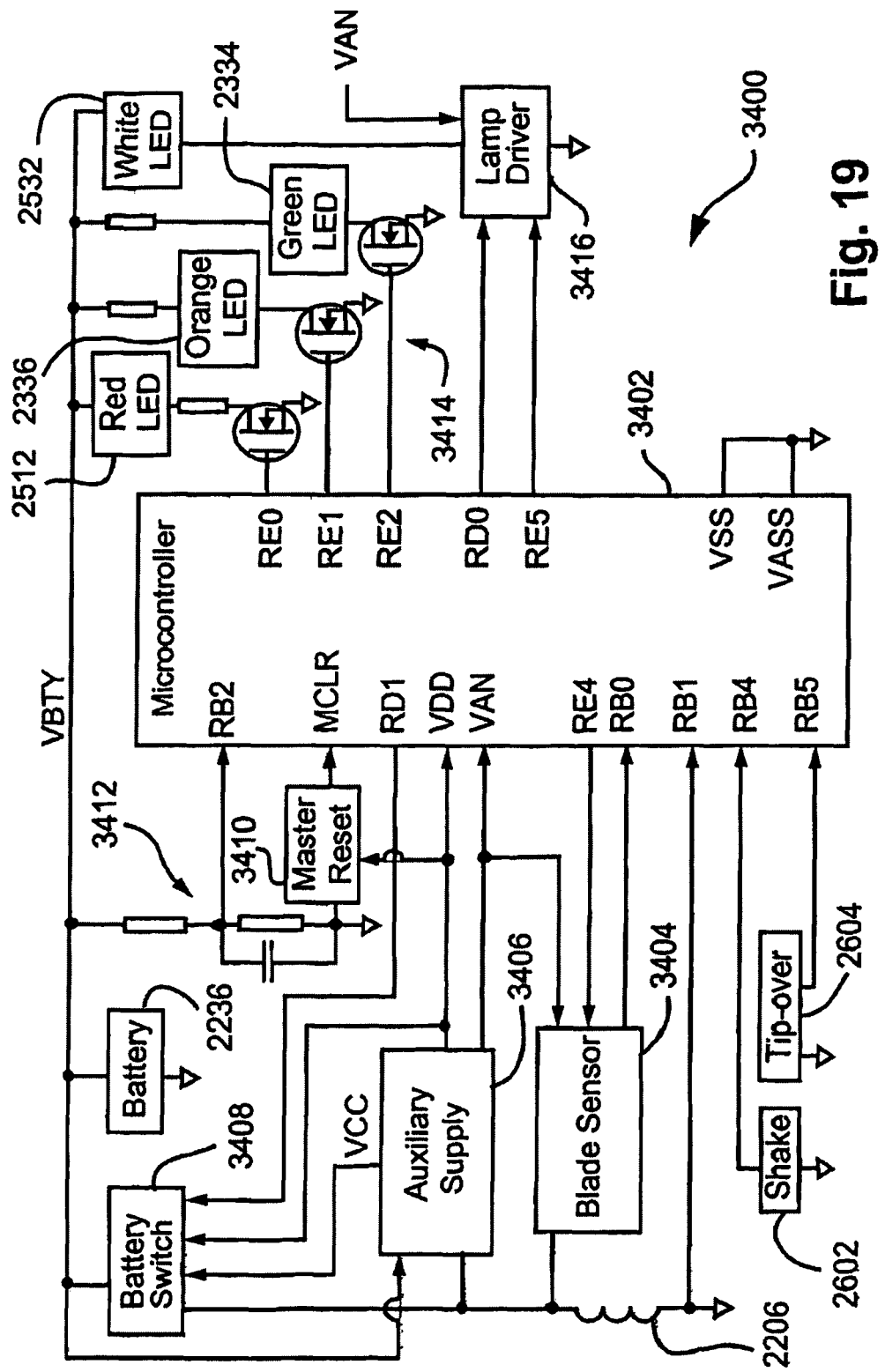
FIG. 19 is a schematic block diagram representation of an alternate circuit useful for the described laryngoscope.

FIG. 19 shows an alternate electronic configuration 3400 for the handle 120. The arrangement 3400 is centred about a microcontroller 3402 which in this particular implementation is formed by a digital signal processor such as a DSPIC30F3011 microcontroller. Such a device features a large number of programmable input and output ports together with PWM control modules and an analogue to digital converter (ADC). The use of the microcontroller 3402 permits simplifications to be made in other parts of the circuitry as will be described. However, in FIG. 19 it is to be observed that where reference numerals are used corresponding to those previously described in respect of alternate arrangements, the same components are used and to which the same description applies. Further, in FIG. 19, not all connections to the microcontroller 3402 are shown. Those connections omitted for clarity include oscillator and clock inputs, the use of which would be well understood by those skilled in the art, as well as unused input/output ports.

As with the previous arrangement of FIG. 7, the circuit 3400 of FIG. 19 includes a sensing coil 2206 which is coupled to each of a blade sensor circuit 3404, an auxiliary supply 3406, and a battery switch 3408.

Figure 17:
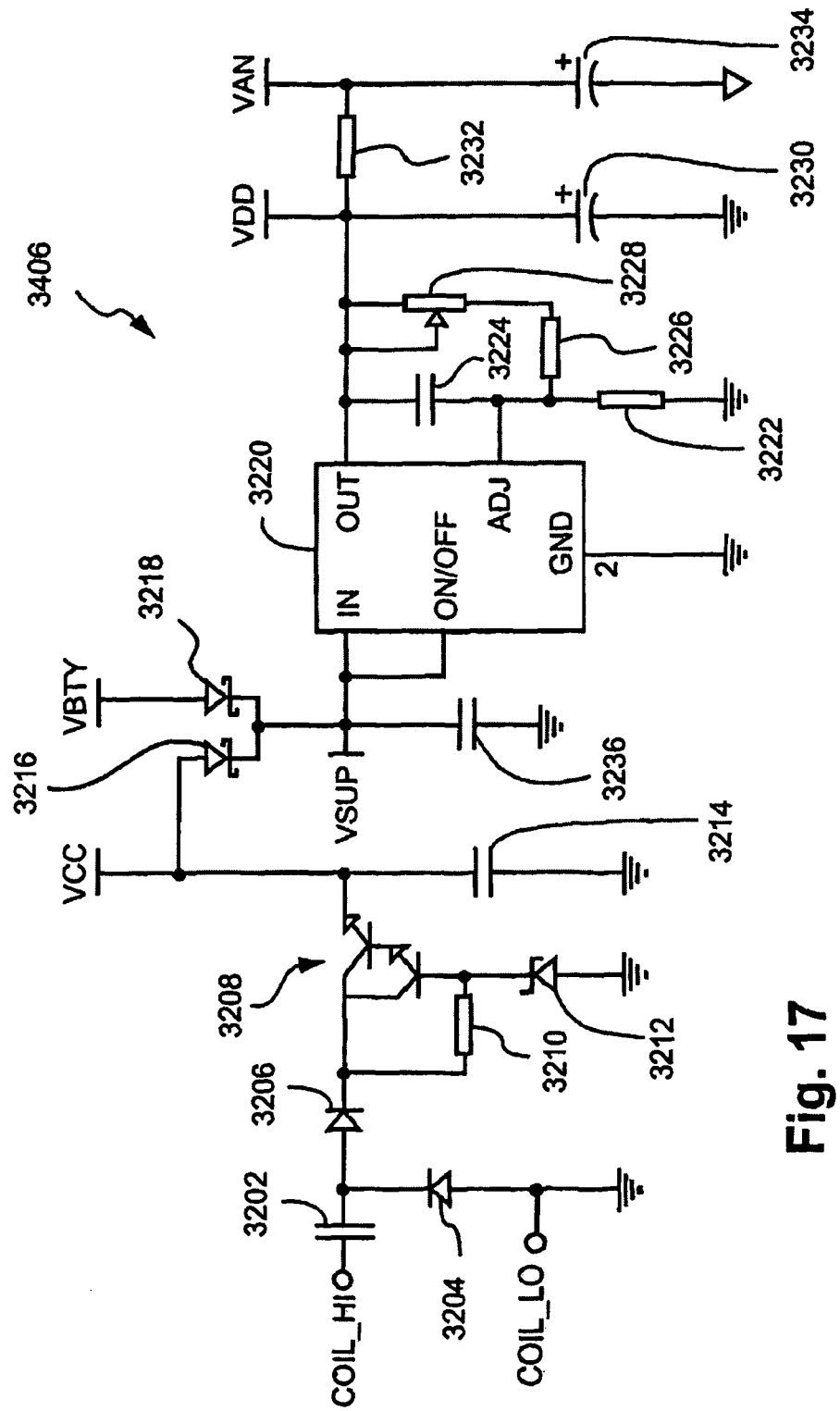
FIG. 17 is a schematic circuit diagram of the auxiliary supply used in the arrangement of FIG. 19.

Firstly, referring to FIG. 17, the auxiliary supply 3406 is seen to include a capacitor 3202 which couples the coil 2206 to a voltage doubler configuration of diodes 3204 and 3206 which supply a simple regulator formed by a zener diode 3212 biased via a resistor 3212 and passing current via a Darlington configuration transistor 3208 to a smoothing capacitor 3214. This provides a voltage VCC which supplies the battery switch 3408 as well as a (Schottky) diode 3216 arranged in parallel with a further (Schottky) diode 3218 deriving power from the battery 2236 via a battery bus VBTY. In the illustrated arrangement Schottky diodes were used due to convenient size and packaging and to reduce the voltage drop between the battery and the regulator. A common cathode connection of the two diodes 3216 and 3218 provides a supply voltage to a smoothing capacitor 3236 and a low current voltage regulator 3220 whose output voltage is adjustable by means of adjustment circuitry formed by resistors 3222, 3226, a capacitor 3224 and a variable resistor 3228. The regulator 3220 provides a voltage output VDD to a smoothing capacitor 3230 which is then further smoothed by a resistor-capacitor filter formed of a resistor 3232 and a capacitor 3234 to provide an analogue supply voltage VAN. The analogue supply voltage VAN is used to power the analogue to digital converter within the microcontroller 3402.

Figure 16:
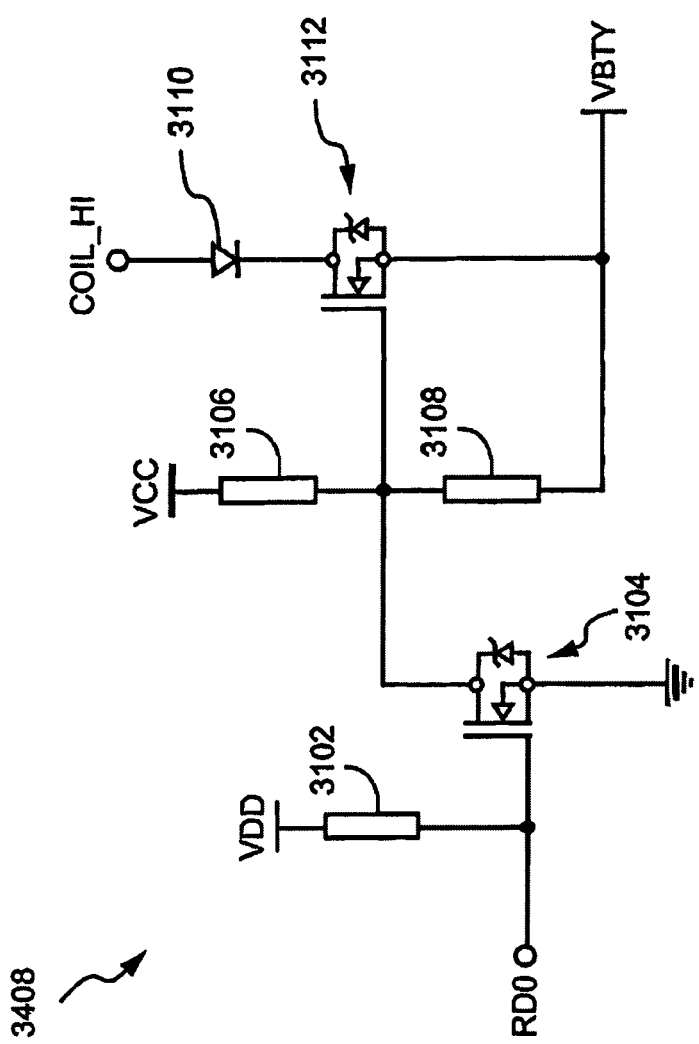
FIG. 16 is a schematic circuit diagram of the battery switch used in the arrangement of FIG. 19.

The battery switch 3408 is seen in FIG. 16 and derives supply inputs from each of VDD, VCC and the coil 2206. The battery switch 3408 receives a switching input from a digital output RD1 of the microcontroller 3402. Output RD1 is an active low which is used to turn off a switching transistor 3104 in turn to enable a primary switching transistor 3112 to enable current to flow via a diode 3110 from the coil 2206 to the battery bus VBTY to thereby charge the battery 2236.

Returning to FIG. 19, coupled to the battery bus VBTY is a battery voltage sensing circuit 3412 incorporating a resistor divider and filter which provides an analogue input RB2 of the microcontroller 3402 to enable the battery voltage to be continually monitored during charging operations and to shut down the handle before the battery is fully discharged (at about 4V). A master reset circuit 3410 couples between the VDD line and an MCLR input of the microcontroller 3402.

Figure 15:
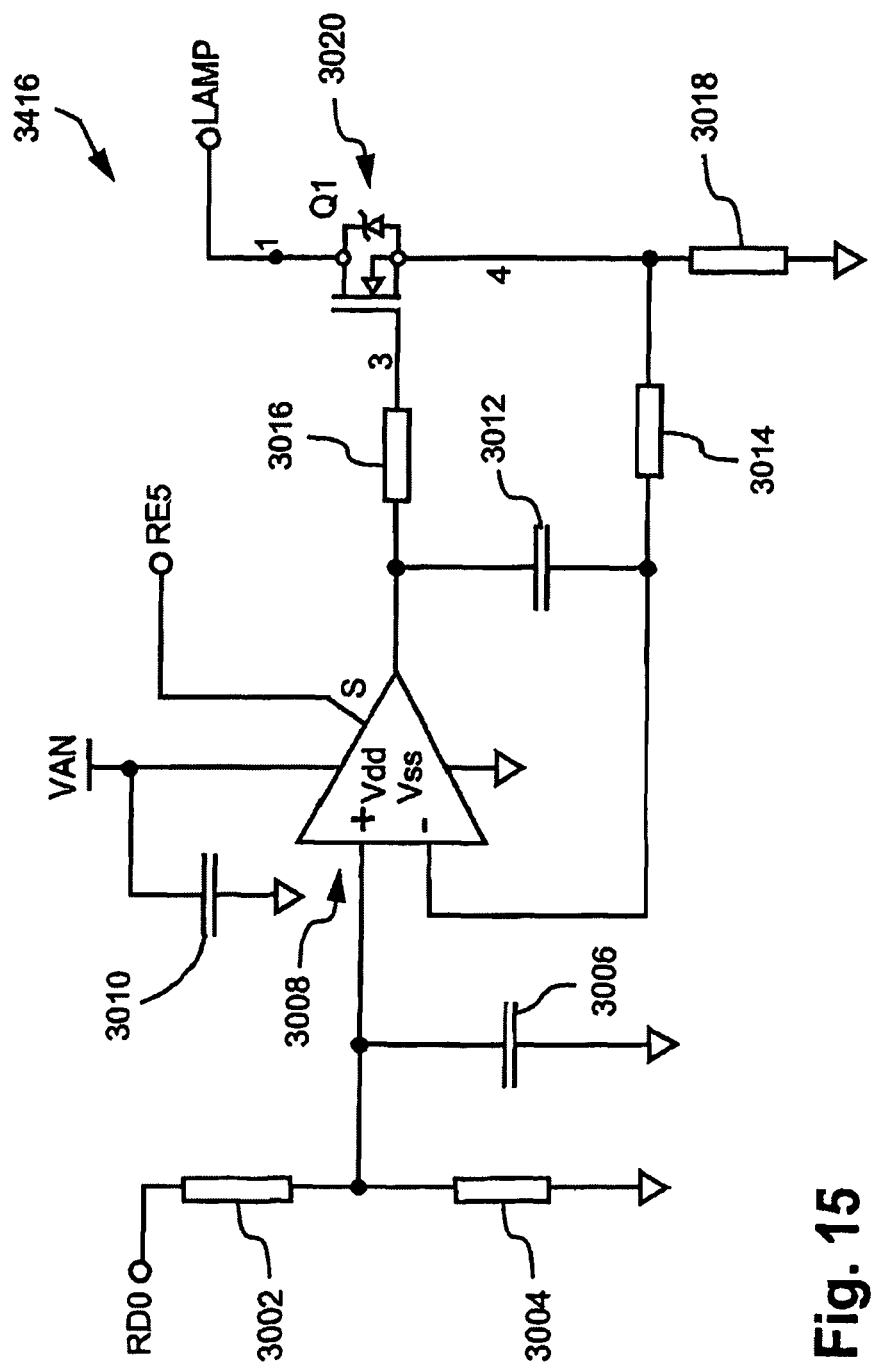
FIG. 15 is a schematic circuit diagram of the white lamp driver used in the arrangement of FIG. 19.

As seen in FIG. 19, each of the traffic light LED's 2512, 2336 and 2334 are supplied by a respective output RE0, RE1 and RE2 of the microcontroller 3402 to a corresponding one of a bank of driver transistors 3414. Accordingly, by enabling each of the outputs RE0-RE2, the corresponding LED's may be illuminated. In this implementation, the red LED 2512 has two roles. Firstly, as in the arrangement of FIG. 10, the red LED 2512 is illuminated by flashing when excessive force is applied to the blade. Further, in the microcontroller implementation the red LED 2512 is also illuminated when the battery capacity has dropped to a level where full illumination (150 mA drain) cannot be maintained for useful period of time, such as a further 20 minutes of operation. Such a period can be quite variable based on many factors. As such the "traffic light" is fully operative to represent the battery state during bother charging and use. The white LED 2532 is driven from a lamp driver 3416 as seen in FIG. 15 and is driven by two outputs RD0 and RE5 of the microcontroller 3402. Specifically, the output RD0 which supplies an input of the lamp driver 3416 is a pulse width modulated (PWM) signal which, through varying the mark-space ratio of that signal can directly vary the output power of the white LED 2532. Accordingly, this functionality can afford a wide range of illumination intensities to be delivered from the white LED and particularly, a full power illumination mode when being used as a laryngoscope, and also a half power mode when being used as a torch, such as in the examples described above. The PWM signal from RD0 supplies a resistor divider formed of resistors 3002 and 3004 together with a smoothing capacitor 3006. This smooths the PWM pulses to supply a smoothed voltage value to the non-inverting input of an operational amplifier 3008. An output of the op-amp 3008 is coupled via a resistor-capacitor network formed of resistors 3014 and 3016 and capacitor 3012, for stability of op-amp 3008, to a transistor 3020 and a current sensing resistor 3018. As a consequence of the operation of the operational amplifier 3008 and negative feedback afforded by the resistor 3014 to the inverting input of the op-amp 3008, a constant current source is formed drawing a current through the lamp (white LED) 2532 proportional to the smoothed voltage output from the divider 3002/3004.

The operational amplifier 3008 also has an input RE5 which is used to shut down operation of the operational amplifier when the lamp is not being used thereby aiding in the conservation of power.

Figure 18:
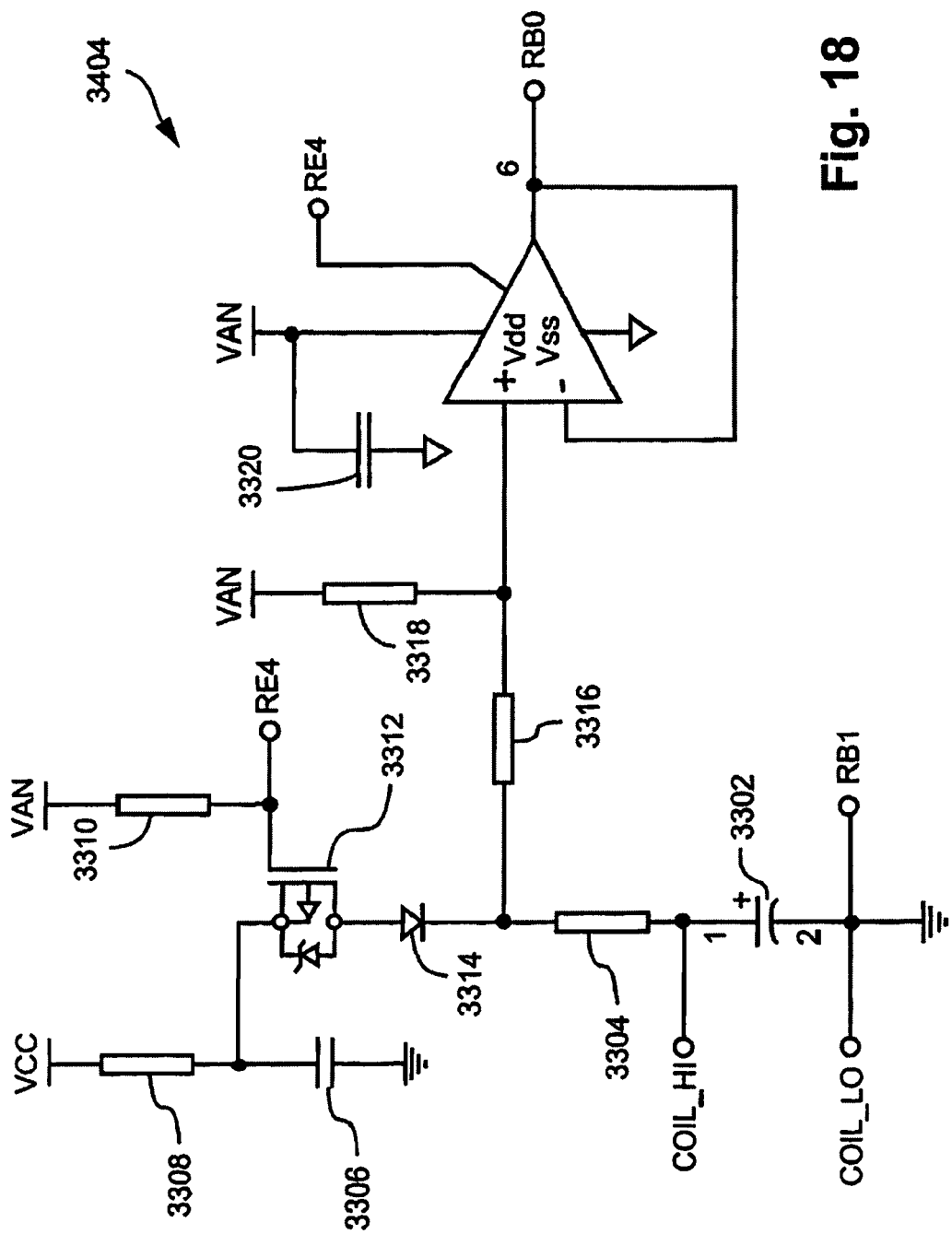
FIG. 18 is a schematic circuit diagram of the blade sensor of the arrangement of FIG. 19.

Turning to FIG. 18, the blade sensor unit 3404 of the present arrangement is substantially simpler than that of the previously described arrangement and operates as follows. A capacitor 3302 is arranged in parallel with the coil 2206 thereby forming a tuned circuit, which is arranged in series with a resistor 3304. A protection diode 3314 couples a current derived from a current source to the resistor 3304. The current source is formed by a transistor 3312 supplied via a resistor 3308 from the VDD line and a smoothing capacitor 3306. A further resistor 3310 couples between the analogue supply voltage VAN and the gate of the transistor 3312 to bias the transistor 3312 "off". In this fashion, an active low control input RE4 output from the microcontroller 3402 is used by the blade sense unit 3404 to switch the transistor 3312 on, thereby delivering a voltage to the diode 3314 and thus the tuned circuit formed by the coil 2206 and capacitor 3302, via the resistor 3304. As such, the value of the resistor 3304 establishes the magnitude of current passing through the tuned circuit 2206/3302.

Figure 31:
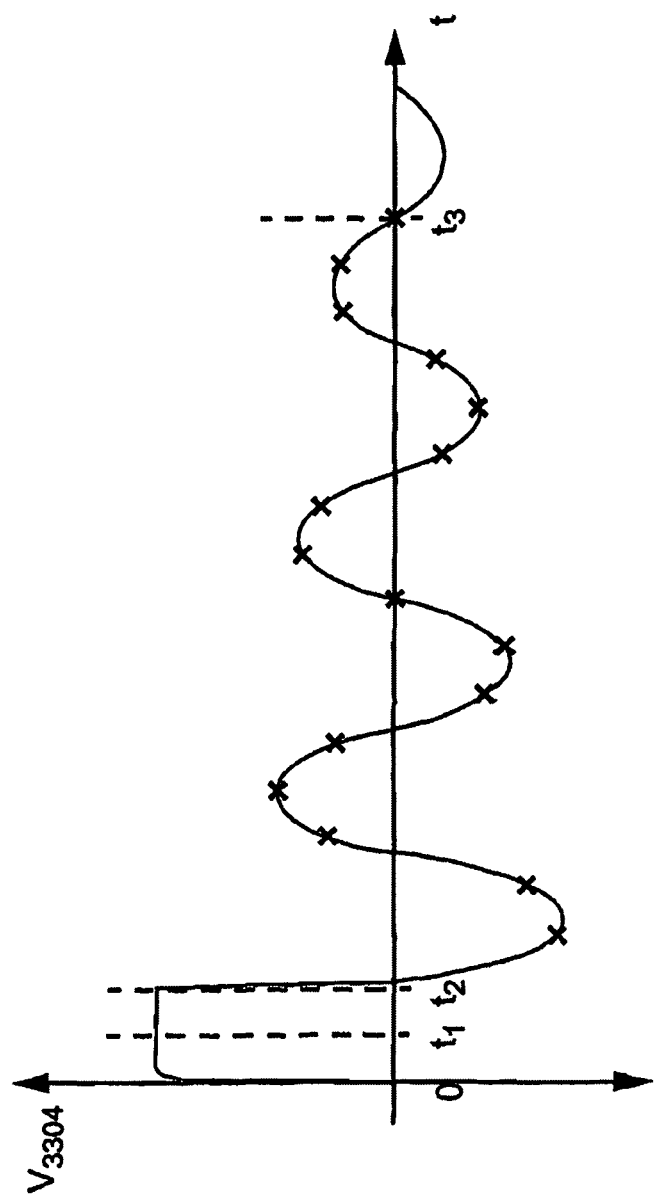
FIG. 31 is a plot of the voltage waveform developed using the circuit of FIG. 18 and detected according to the flowchart of FIG. 23.

Initially, the input RE4 is disabled (goes active low) which turns on the transistor 3312 allowing current to flow through the diode 3314, the resistor 3304 and into the tuned circuit formed by the coil 2206 and the capacitor 3302. Since the capacitor 3302 is initially discharged, the voltage on the capacitor 3302 will rise and may even incorporate a slightly ringing component until such time as the voltage upon the capacitor 3302 stabilises to a steady state DC voltage. This rise, without the ringing, is seen in the plot of the voltage on resistor 3304 in FIG. 31, during the time between 0 and $t_1$. After a steady state period between $t_1$ and $t_2$, the input RE4 is disabled at time $t_2$ (taken to a logic high value) which switches off the transistor 3312. The voltage drops rapidly as the capacitor 3302 then commences to discharge into the coil 2206. This causes the tuned circuit to ring and oscillate with a decaying magnitude, as illustrated in FIG. 30 between times $t_2$ and $t_3$. The ringing decaying magnitude signal is sensed by a voltage follower amplifier 3322 via a resistor 3316 and provided to an analogue input RB0 of the microcontroller 3402. The microcontroller 3402 can then examine the decaying oscillating signal to determine its magnitude. The ringing magnitude which will vary (decay more rapidly) according to the amount of load placed upon the tuned circuit 2206/3302, for example when the electromagnetically coupled to the coil 136 within the blade 130, or the blades 160, 170 or 180. The voltage follower 3322 includes a further input RE4 which is used to shut down that device when not in use.

FIGS. 20 to 28 show various state diagram and flowcharts representing the control program executing within the microcontroller 3402 for operation of the handle 120 using the circuit of FIG. 19. Typically, the control program is configured to run once every 100 milliseconds thereby conserving battery power when not in use. The overall program typically runs for approximately 2 to 3 milliseconds depending upon the particular task being performed.

Figure 21:
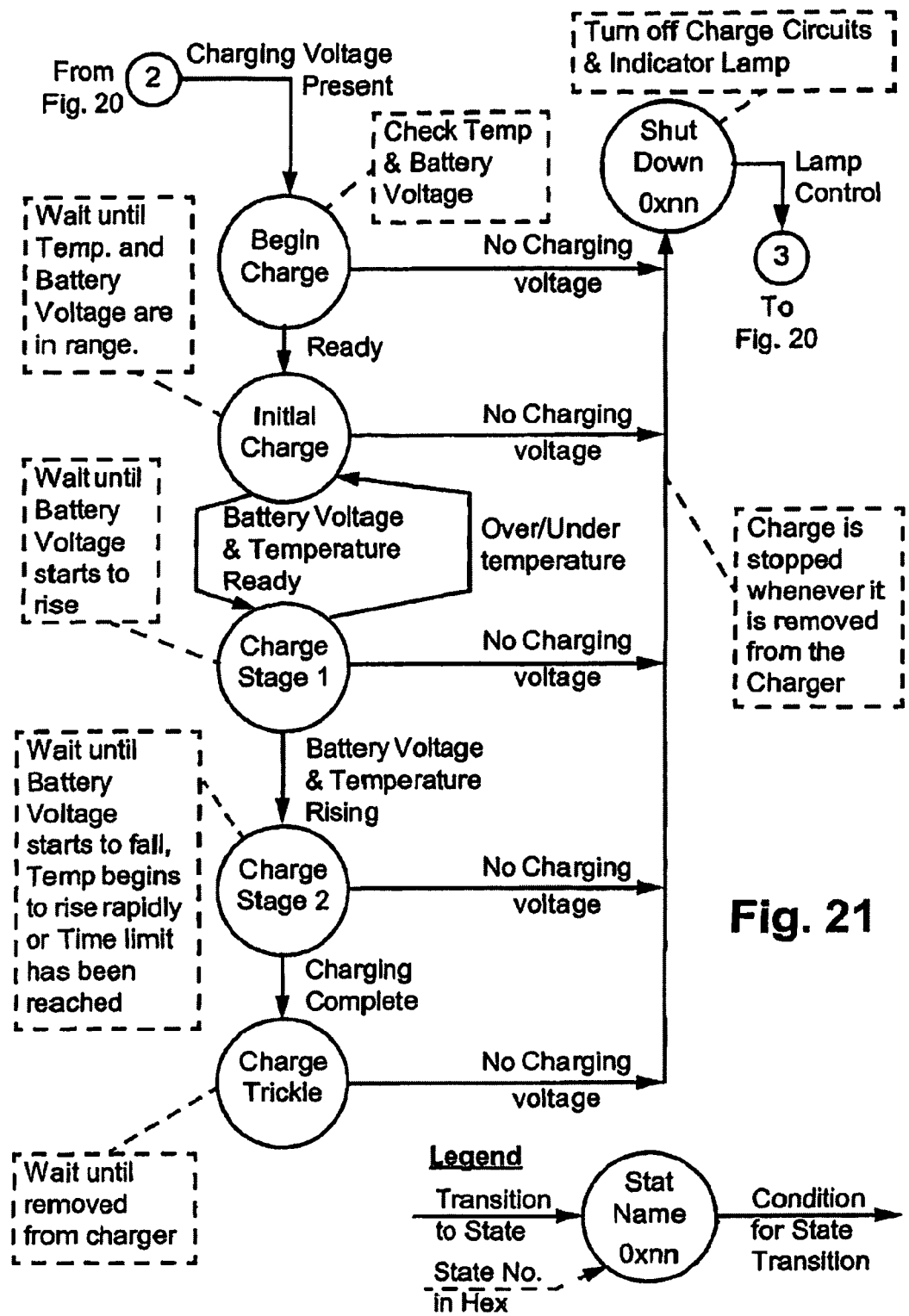
FIG. 21 is a state variable diagram of the battery charging operation of the arrangement of FIG. 19.

FIG. 20 shows a state diagram representing the reset of the microcontroller 3402 at state 1 which carries forward to a "start" position. If a charging voltage is detected, state 2 is entered as seen in FIG. 21. The start position is also returned to from state 3, also seen in FIG. 21, when the charging voltage is removed. If there is no charging voltage present, the white lamp 2532 is deemed to be off, "lamp off". Subsequent shake sensing causes a "torch timer" to be enabled. This turns the lamp on in a torch mode for a timed period. If the blade is sensed, the lamp is turned on, "lamp on", in full-power mode. Further, when an excessive force is sensed, the lamp is flashed, "flash on". After the lamp is illuminated with the blade being sensed, tipping over the laryngoscope 110 can cause the blade timer to timeout thus extinguishing the lamp. This may be the case for example during a lengthy operation where the laryngoscope remains inserted into the patient's airway but illumination is not required. In FIG. 20, the timing values for the blade timer and the torch timer are preferably 4 and 5 minutes respectively. The flash speed is 100 milliseconds. Each of these periods is programmable, and most desirably a whole multiple of the main loop time, discussed with respect to FIG. 25.

FIG. 21 shows the battery charging routine where when a charging voltage is present, battery charging begins at which time the battery voltage is checked along with the temperature. At any time when there is no charging voltage, the circuit is shut down and returns to the state 3 in FIG. 20. Once the battery temperature and voltage are in range, and initial charge is commenced. Battery charging then proceeds through two stages whereby the battery voltage and temperature continue to be monitored. At that time in which the battery voltage starts to fall and temperature begins to rise, the battery is deemed to fully charged and the charger enters a trickle charge mode.

Figure 22:
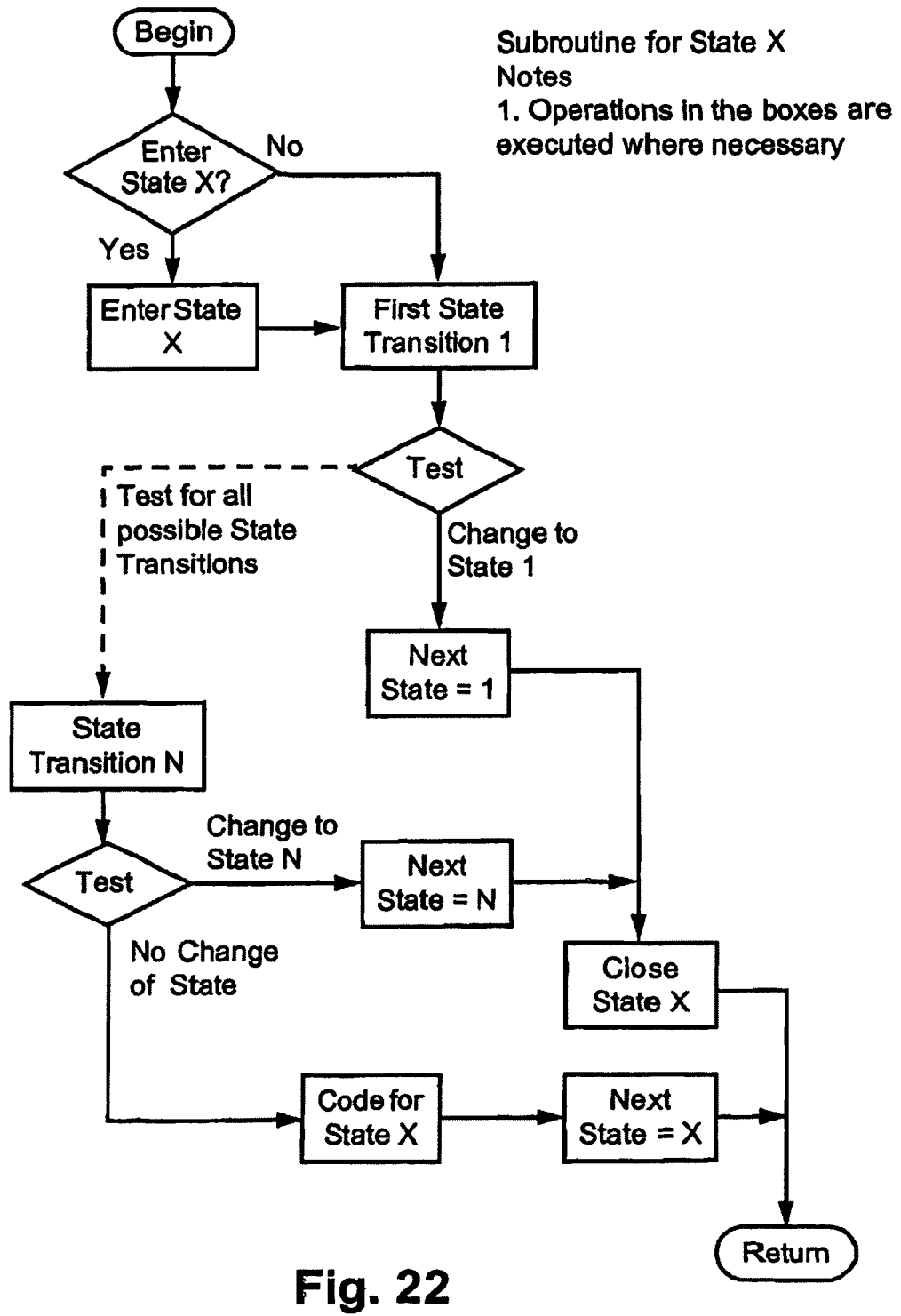
FIG. 22 is a flowchart useful in developing the arrangement of FIG. 19

FIG. 22 shows a generalised flowchart for any state as used in the microcontroller 3402. This form of subroutine can be applied to any type of physical state and testing procedures required for that state. This is entered every 100 milliseconds, such that the flash speed for example is set by the speed of operation of the code of FIG. 22.

Figure 23:
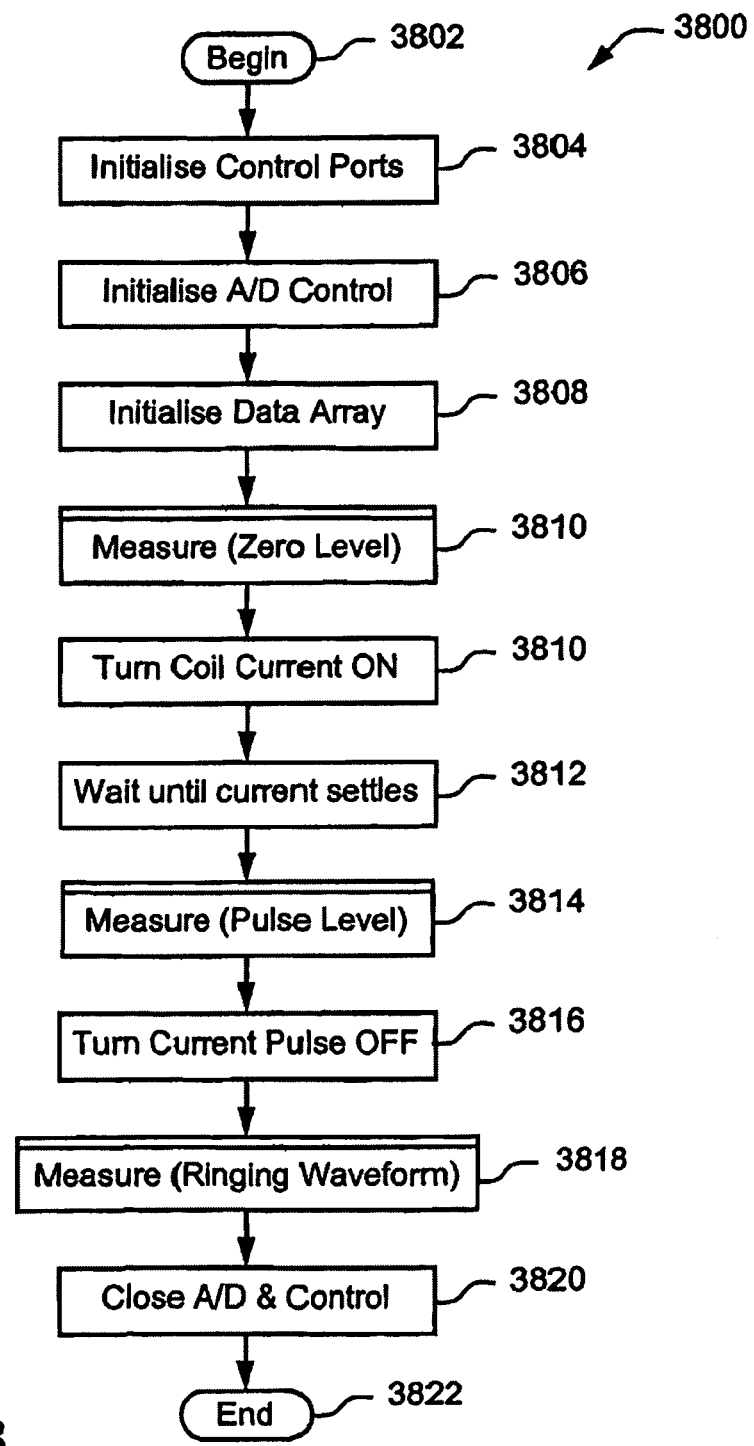
FIG. 23 is a flowchart of a first stage of blade sense pressure measurement.

FIG. 23 shows a flowchart of a procedure 3800 for blade sensing. In step 3802, control ports are initialised, and in step 3806 analogue to digital conversion within the microcontroller 3402 is initialised. A data array is then also initialised in step 3810 and in step 3810 the analogue to digital converter within the microcontroller 3402 measures a zero level at port RB0 (FIGS. 18 and 19). This is done for referencing purposes. At this stage, the current in the coil 2206 is then enabled by turning on the transistor 3312 via port RE4 as described above. Once the current through the circuit settles, a measure is taken at step 3814 of the value of RB0 representing the maximum pulse level. The current is turned off at step 3816 by disabling RE4 which then causes the tuned credit to ring, the voltage output of which is then measured via RB0 at step 3818. Once the waveform has settled, analogue to digital control is ended at step 3820 and the procedure 3800 ends at step 3822.

Figure 24:
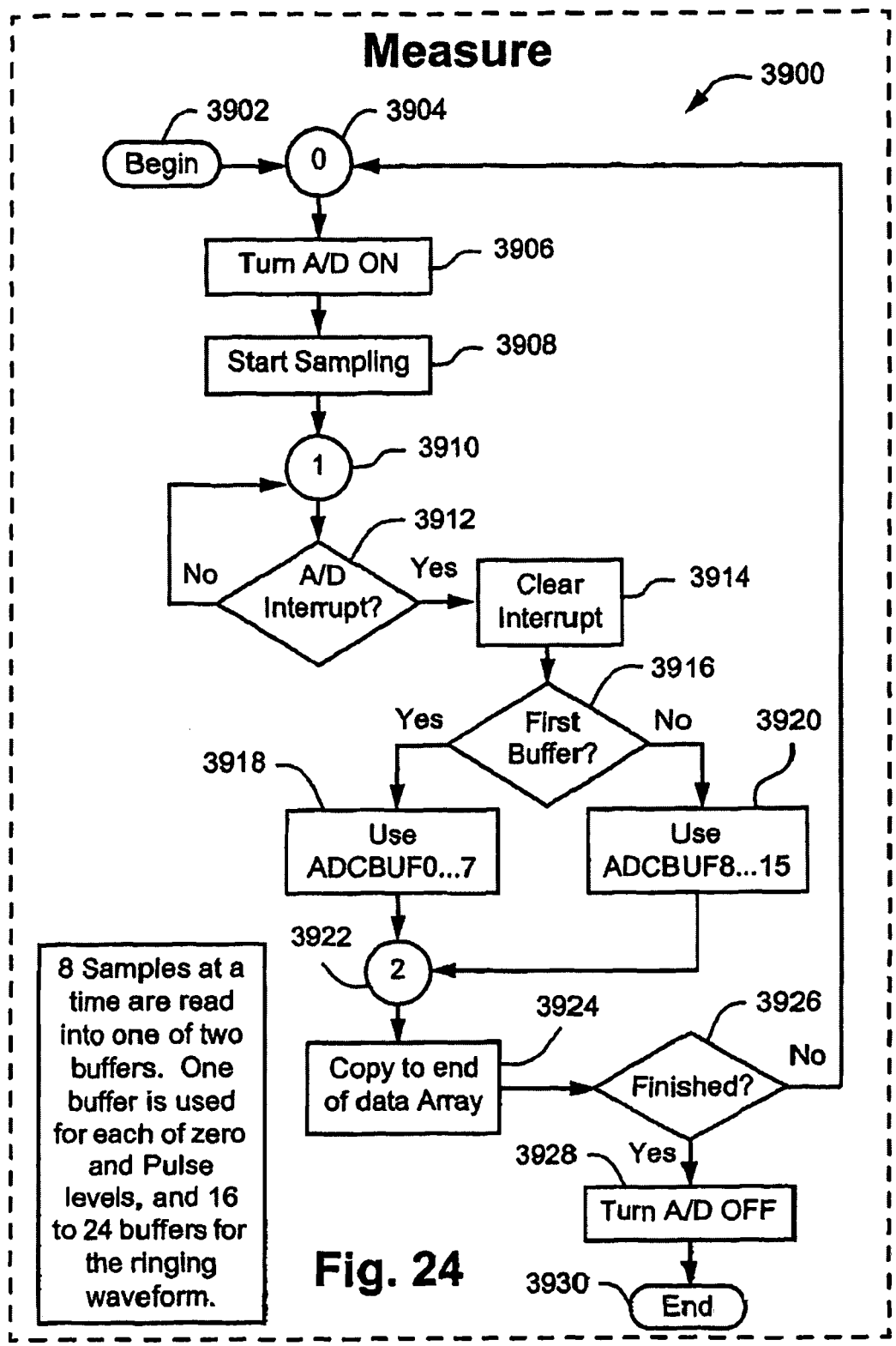
FIG. 24 is a flowchart of a measurement of responses to the first stage of FIG. 23.

FIG. 24 shows the procedure 3900 performed within the microcontroller 3402 for measuring the waveform output on RB0 from the blade sensing unit 3404 as performed at step 3818. The procedure 3900 has a begin step 3902 and a first loop return 3904. Initially, the analogue to digital converter is turned on in step 3906 and it then starts sampling at step 3908. Exemplary sample points are shown in FIG. 30 and sampling occurs at a rate greater than 200K samples/second, and preferably at about 300K samples/second. A test is determined at step 3912 for any A to D interrupts and if there is no such interrupt, control returns to loop node 3910 between steps 3908 and 3912 and sampling continues. Where an interrupt occurs and is detected in step 3912, the interrupt is then cleared in step 3914 and the status of a first buffer is tested in step 3916. If the first buffer has available memory, samples are placed in the various ADC buffers 0.7 in step 3918. When that first series of buffers is full, step 3916 directs storage into ADC buffers 8 . . . 15 in step 3920 are then used. Once the 16 samples are obtained from the measurement, control returns via node 3922 to step 3924 where the data from the ADC buffers is copied to a data array. Step 3926 tests whether or not measurements are finished. If not, control returns to node 3904. When finished in step 3926 the ADC is turned off in step 3928 and the measurement procedure 3900 ends at step 3930.

Using the measured values of zero (step 3810) the steady state pulse level (step 3814,) and the measured ringing values (step 3820/3900), the data in the array may then be analysed, by interpolation for example, to determine the magnitude of the ringing waveform. A specific approach can involve full-wave rectification of the waveform, summing the absolute value of the samples and determine the average. The microcontroller 3402 can the compare that measured power against a pre-recorded values for no connection to the blade 130 and connection with threshold force to determine equivalents of the "blade" and "force" signals of the previous arrangement of FIG. 19.

Figure 25:
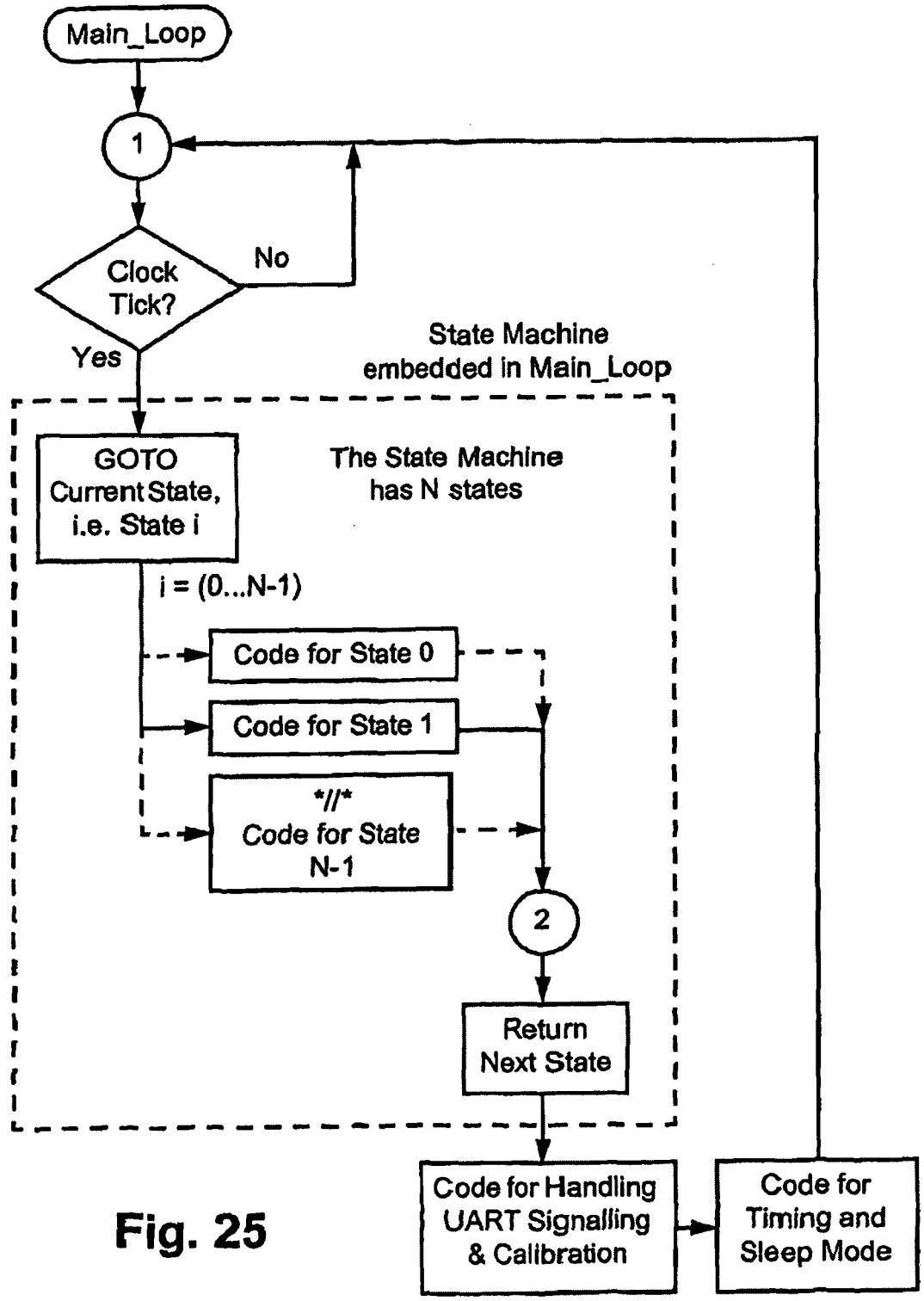
FIG. 25 is flowchart of a main operating loop for the arrangement of FIG. 19.

FIG. 25 shows a flowchart for the main operating loop of the circuit 3400. Initially, a clock for timing a sleep mode is operated and runs in a loop until such time as a clock tick is sensed. At this stage, the state machine is embedded in the main loop implements each of the various stages of the overall state machine of FIG. 20. When all states have been processed, the timing mode is then recommenced. The main loop cycles every 100 milliseconds making this a convenient period for the various timers, which can thus be implemented by counters of the main loop cycle. In FIG. 25, the UART is only shown for completeness and is not used in normal operation. The UART is used during testing and calibration.

Figure 26:
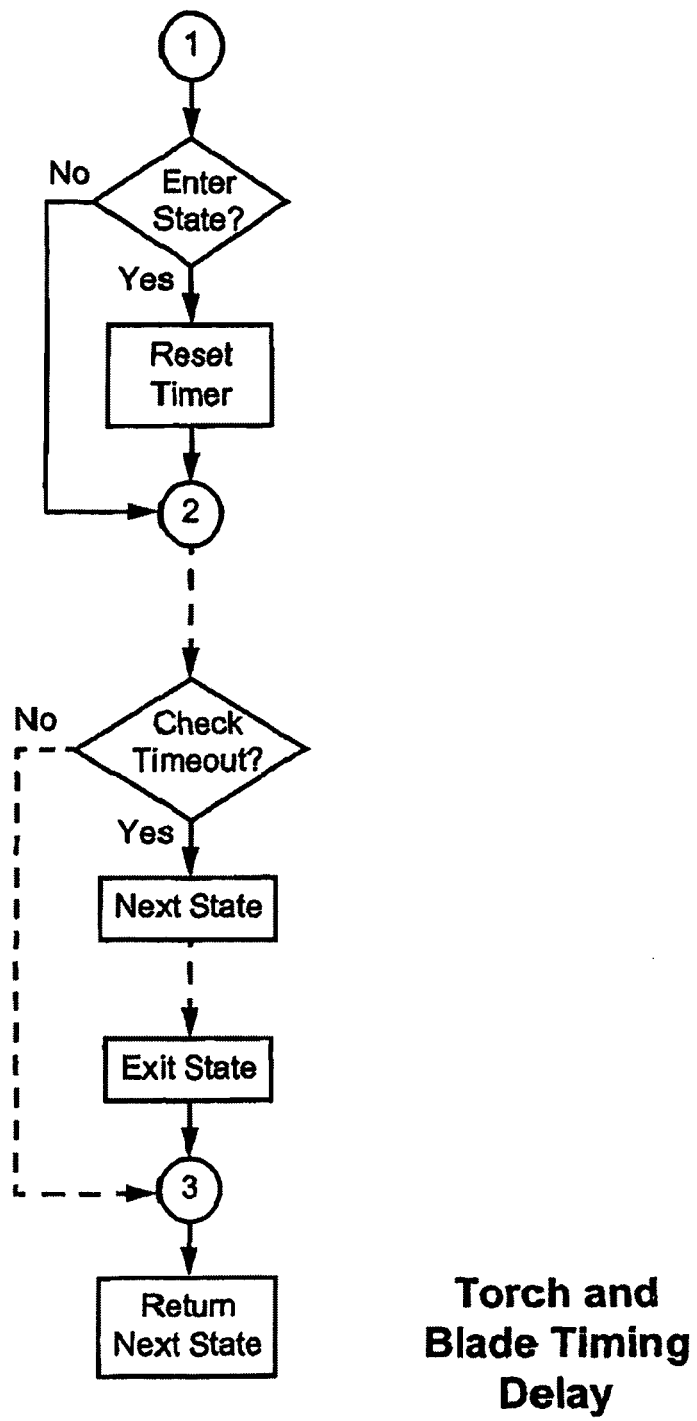
FIGS. 26-28 show flowcharts for operation of various processes in the arrangement of FIG. 19.

FIG. 26 shows a flowchart for the states for torch and blade timing delays. Initially, a test is determined whether or not the state has been entered and if so, the timer is reset. The timer then automatically starts counting. If the timer is timed out, the next state is then processed. If the timer has not timed out, the control flow returns to the next state.

Figure 27:
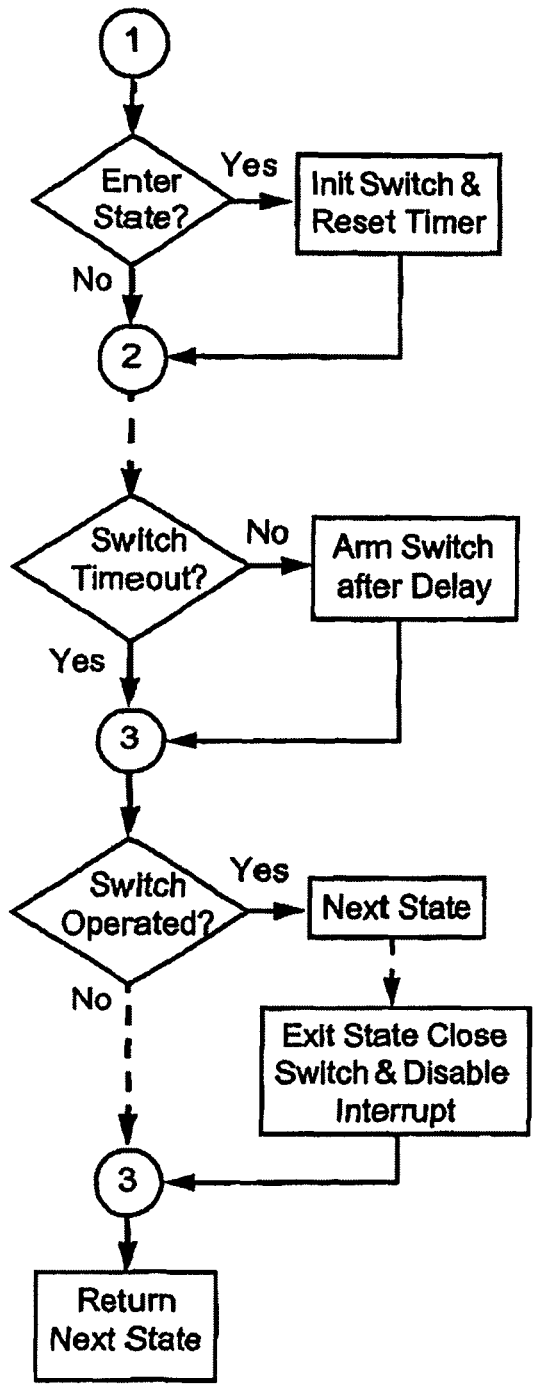
Figure 28:
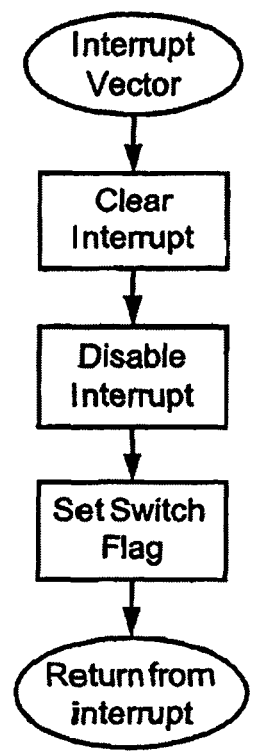

As seen in FIG. 19 and in FIGS. 27 and 28, the shake and tip over switches 2602 and 2604 each directly input to inputs RB4 and RB5 respectively. FIGS. 27 and 28 show routines used for handling each of those inputs to effectively achieve the debounce functionality of the previously described arrangements. As seen in FIG. 27, a state is entered which initialises the switch and resets the timer. This then tests for the switch being actuated. If the switch has timed out, the switch is then armed after a certain period of delay. If the switch is operated, the next state is then enacted. If no switch is operation occurs within the armed period, the routine returns to the next state.

FIG. 28 shows an interrupt service routine for the shock switch whereby when an interrupt vector is received, the interrupt is cleared and then disabled. The restive switch flag is then set and the interrupt returned from. Accordingly, with the arrangements of FIGS. 27 and 28, each of the switches 2602 and 2604 in the arrangement of FIG. 19 are effectively debounced with appropriate flags being set upon actuation.

It will be apparent from the foregoing that the arrangement of FIG. 19 offers an alternate to that previously described in FIGS. 7-12 in terms of overall control through greater levels of programming as well as a reduction in component count and the circuit complexity. Functionalities also improve through simplification of the blade sensor, the ability to implement software routines for battery management, and for full programmable control of white lamp output power.

The foregoing described only a number of embodiments of the present invention and modifications may be made thereto without departing from the scope of the present invention.

For example, whilst the describe embodiments relate to laryngoscopes, the same principles may be applied to other devices, and not just medical devices. For example, the blade 130 may be replaced by an endoscope which may be useful in inspection of the body or of equipment. The arrangements described have significant utility where single use of the implement coupled to the handle is desired, such as in medical applications. Another application may be in the use of a medical waveguide for conveying electromagnetic radiation into a patient for the treatment of tumours and the like.

The claims defining the invention are as follows:

1. A laryngoscope apparatus comprising:
a laryngoscope handle with a coupling region; and
a laryngoscope blade, the laryngoscope handle and the laryngoscope blade being adapted to be releasably operatively connectable at a coupling region of the laryngoscope blade to the coupling region of the laryngoscope handle to form a laryngoscope;
wherein:
the laryngoscope handle comprises a sensing coil arranged at the coupling region of the laryngoscope handle, and a sensing circuit connected to the sensing coil;
the laryngoscope blade comprises:
a detection coil arranged at the coupling region of the laryngoscope blade, and via interaction of the coupling region of the laryngoscope handle and the coupling region of the laryngoscope blade to thereby associate the sensing coil and the detection coil;
an elongate extension insertable into a mouth of a patient when the laryngoscope is in use; and
a tubular coupling arrangement containing the detection coil, into which the coupling region of the laryngoscope handle can be positioned to form the laryngoscope, the laryngoscope blade being configured to be disposable after use;
the sensing circuit is configured:
during connection of the laryngoscope blade to the laryngoscope handle to form the laryngoscope, to detect coupling of the laryngoscope handle to the laryngoscope blade through a change in an electrical signal imparted upon the sensing coil caused by electromagnetic interaction of the detection coil with the sensing coil; and
when the laryngoscope is formed and in use, to detect a force applied to the laryngoscope blade according to changes in an electromagnetic coupling between the sensing coil and the detection coil, the laryngoscope blade being configured such that when the force is applied to the laryngoscope blade, the force changes the electromagnetic coupling between the detection coil and the sensing coil relative to the force;
the coupling region of the laryngoscope handle is cylindrical and contains the sensing coil and a lamp, the lamp being energizable upon detecting coupling of the laryngoscope blade to the laryngoscope handle; and
the laryngoscope handle further comprising an indicator device comprising an arrangement of LEDs, the arrangement of LEDs being electrically associated with the sensing circuit to provide a user of the laryngoscope with an indication of the detected force applied to the laryngoscope blade relative to a determined threshold.

2. The laryngoscope apparatus according to claim 1 wherein the electrical signal comprises an oscillation imparted upon the sensing coil and having an oscillation power modified at least by electromagnetic coupling of the sensing coil with the detection coil.

3. The laryngoscope apparatus according to claim 2 wherein the laryngoscope handle further comprises an arrangement which is configured such that the oscillation power is further modified in response to detection of the force beyond a predetermined value being imparted upon the laryngoscope blade.

4. The laryngoscope apparatus according to claim 3 wherein the laryngoscope blade comprises at least one switch connected electrically to the detection coil to change loading of the coupling between the sensing and detection coils, the at least one switch being actuable in response to the force.

5. The laryngoscope apparatus according to claim 4 wherein the laryngoscope handle further comprises a capacitance arranged in parallel with the sensing coil to form a tuned load, the sensing circuit comprising an oscillator arrangement configured to form the electrical signal in the tuned load and a detection arrangement configured to detect a magnitude of oscillation, wherein the oscillator arrangement comprises an oscillator circuit outputting to and having a magnitude determined at least by the tuned load and wherein the detection arrangement comprises at least one comparator for comparing a corresponding voltage reference against a voltage that varies with a power consumed by the electromagnetic coupling between the sensing coil and the detection coil.

6. The laryngoscope apparatus according to claim 5 wherein the oscillator arrangement comprises a switch arranged to supply current to energize the sensing coil to a measurable value, the switch being operable to cease supply of the current to cause the tuned load to thereby oscillate forming the electrical signal with a decreasing magnitude, and the detection arrangement comprises a processor circuit for determining a magnitude of oscillation of the electrical signal.

7. The laryngoscope apparatus according to claim 6 wherein the processor circuit comprises a means for sampling the electrical signal and from samples measuring the magnitude of oscillation, and a comparator arrangement for comparing the magnitude of oscillation measured by the processor circuit against a first reference for indicating an operative coupling between the laryngoscope handle and the laryngoscope blade, and for comparing the magnitude of oscillation against at least a second reference for indicating the force in excess of the predetermined value being applied to the laryngoscope blade.

8. The laryngoscope apparatus according to claim 7 further comprising the indicator device indicates when the force exceeds the second reference.

9. The laryngoscope apparatus according to claim 5 wherein the detection arrangement comprises a first comparator arrangement for indicating an operative coupling between the laryngoscope handle and the laryngoscope blade, and a second comparator arrangement for indicating the force is in excess of the predetermined value being applied to the laryngoscope blade.

10. The laryngoscope apparatus according to claim 9 further comprising the indicator device indicates when the force exceeds the predetermined value.

11. The laryngoscope apparatus according to claim 4 wherein the laryngoscope blade includes a barrel associated with the coupling region of the laryngoscope blade upon which the detection coil is formed, the barrel being movable relative to the sensing coil in response to the force to change the coupling between the sensing and detection coils.

12. The laryngoscope apparatus according to claim 4 wherein the at least one switch comprises two electrical contact layers separated by a perforated insulating layer, the two electrical contact layers contacting each other through the perforated insulating layer when subjected to the force.

13. The laryngoscope apparatus according to claim 1 wherein the coupling of the laryngoscope handle to the laryngoscope blade provides for the sensing coil and the detection coil to be substantially co-axial and the sensing coil to be positioned within the detection coil.

14. The laryngoscope apparatus according to claim 1, further comprising a charger module, the charger module comprising a power supply connected to a tuned circuit,
wherein:
the laryngoscope handle further comprises a power circuit connected to the sensing coil, the power circuit being configured to charge a battery of the laryngoscope handle upon sensing a current induced in the sensing coil; and
the laryngoscope handle is configured to be removably retained by the charger module, the power supply providing the current induced in the sensing coil by interaction of the sensing coil with the tuned circuit of the charger module when the laryngoscope handle is retained by the charger module.

15. The laryngoscope apparatus according to claim 14 wherein the power circuit is configured to operate such that the current induced in the sensing coil when the laryngoscope handle is inserted into a charger module, is received, rectified and used to charge the battery of the laryngoscope handle.

16. The laryngoscope apparatus according to claim 15 wherein the laryngoscope handle further comprises at least one electrical load controllably energized by the battery and operable upon detection of coupling of the laryngoscope handle to the laryngoscope blade.

17. The laryngoscope apparatus according to claim 16 wherein the at least one electrical load comprises a lamp arranged to emit light from the laryngoscope blade when the laryngoscope is formed.

18. The laryngoscope apparatus according to claim 1, wherein the detection coil comprises a single closed turn.

* * * * *